US006805125B1

(12) United States Patent
Crump et al.

(10) Patent No.: US 6,805,125 B1
(45) Date of Patent: *Oct. 19, 2004

(54) RESPIRATORY SUCTION CATHERER APPARATUS

(75) Inventors: Chet M. Crump, Draper, UT (US); Edward B. Madsen, Riverton, UT (US); V. Roland Smith, Salt Lake City, UT (US)

(73) Assignee: Ballard Medical Products, Draper, UT (US)

( * ) Notice: Subject to any disclaimer, the term of this patent is extended or adjusted under 35 U.S.C. 154(b) by 10 days.

This patent is subject to a terminal disclaimer.

(21) Appl. No.: 09/693,261

(22) Filed: Oct. 20, 2000

Related U.S. Application Data

(63) Continuation of application No. 09/357,591, filed on Jul. 20, 1999, now Pat. No. 6,227,200, which is a continuation-in-part of application No. 09/157,605, filed on Sep. 21, 1998, now abandoned.

(51) Int. Cl.[7] .......................... A61N 16/00; A62B 9/02; A62B 9/06
(52) U.S. Cl. .................... 128/207.16; 128/207.14; 128/910; 128/912
(58) Field of Search ....................... 128/207.14, 207.16, 128/910, 912; 604/35, 171; 239/396, 490, 491, 494, 496, 497

(56) References Cited

U.S. PATENT DOCUMENTS

| | | | |
|---|---|---|---|
| 3,240,431 A | * | 3/1966 | Hug et al. ................... 239/490 |
| 3,710,942 A | | 1/1973 | Rosenberg |
| 3,831,629 A | | 8/1974 | Mackal et al. |
| 3,834,388 A | | 9/1974 | Sauer |
| 3,902,500 A | | 9/1975 | Dryden |
| 3,937,220 A | | 2/1976 | Coyne |

(List continued on next page.)

OTHER PUBLICATIONS

Hudson RCI advertisement for "Cath–Guide", 1996.

*Primary Examiner*—Henry Bennett
*Assistant Examiner*—Joseph F. Weiss
(74) *Attorney, Agent, or Firm*—Dority & Manning, P.A.

(57) ABSTRACT

An improved respiratory suction apparatus—catheter includes a manifold for attachment to the distal hub of an endotracheal tube to form a respiration circuit, a catheter tube which is displaceable through the manifold and into the endotracheal tube to suction secretions from the tube and lungs, and a valve mechanism disposed adjacent the respiration circuit to minimize the draw of air from the respiration circuit of a patient while the catheter is being cleaned. In a preferred embodiment of the invention, the catheter is cleaned more thoroughly than in the prior art while simultaneously drawing little or no air from the patient's respiration circuit.

41 Claims, 19 Drawing Sheets

U.S. PATENT DOCUMENTS

| | | | |
|---|---|---|---|
| 3,991,762 A | 11/1976 | Radford | |
| 4,015,336 A | 4/1977 | Johnson | |
| 4,047,527 A | 9/1977 | Kelsen | |
| 4,193,406 A | 3/1980 | Jinotti | |
| 4,351,328 A | 9/1982 | Bodai | |
| 4,468,224 A | 8/1984 | Enzmann et al. | |
| 4,510,933 A * | 4/1985 | Wendt et al. | 128/207.14 |
| 4,516,573 A | 5/1985 | Gedeon | |
| 4,529,003 A | 7/1985 | Iannuzzelli et al. | |
| 4,569,344 A | 2/1986 | Palmer | |
| 4,573,965 A | 3/1986 | Russo | |
| 4,573,979 A | 3/1986 | Blake | |
| 4,574,173 A | 3/1986 | Bennett | |
| 4,595,005 A | 6/1986 | Jinotti | |
| 4,622,964 A | 11/1986 | Flynn | |
| 4,638,539 A | 1/1987 | Palmer | |
| 4,649,913 A | 3/1987 | Watson | |
| 4,657,008 A | 4/1987 | Broddner et al. | |
| 4,691,702 A | 9/1987 | Chantzis | |
| 4,696,305 A | 9/1987 | von Berg | |
| 4,705,073 A | 11/1987 | Beck | |
| 4,834,726 A | 5/1989 | Lambert | |
| 4,909,248 A | 3/1990 | McLennan Anderson | |
| 4,929,426 A | 5/1990 | Bodai et al. | |
| 4,967,743 A | 11/1990 | Lambert | |
| D312,880 S | 12/1990 | Bodai et al. | |
| 5,005,568 A | 4/1991 | Loescher et al. | |
| 5,060,646 A | 10/1991 | Page | |
| 5,064,122 A * | 11/1991 | Kamishita et al. | 239/396 |
| 5,073,164 A | 12/1991 | Hollister et al. | |
| 5,083,561 A | 1/1992 | Russo | |
| 5,088,486 A | 2/1992 | Jinotti | |
| 5,107,829 A | 4/1992 | Lambert | |
| 5,125,893 A | 6/1992 | Dryden | |
| 5,134,996 A | 8/1992 | Bell | |
| 5,139,018 A | 8/1992 | Brodsky et al. | |
| 5,140,983 A | 8/1992 | Jinotti | |
| 5,158,569 A | 10/1992 | Strickland et al. | |
| 5,184,611 A | 2/1993 | Turnbull | |
| 5,191,881 A | 3/1993 | Beck | |
| 5,213,096 A | 5/1993 | Kihlberg et al. | |
| 5,215,522 A | 6/1993 | Page et al. | |
| 5,220,916 A | 6/1993 | Russo | |
| 5,224,471 A * | 7/1993 | Marelli et al. | 128/200.14 |
| 5,230,332 A | 7/1993 | Strickland | |
| 5,242,084 A | 9/1993 | Jinotti | |
| 5,254,098 A | 10/1993 | Ulrich et al. | |
| 5,255,676 A | 10/1993 | Russo | |
| 5,277,177 A | 1/1994 | Page et al. | |
| 5,300,043 A | 4/1994 | Devlin et al. | |
| 5,305,762 A * | 4/1994 | Acorn et al. | 128/200.24 |
| 5,309,902 A | 5/1994 | Kee et al. | |
| 5,309,904 A | 5/1994 | Beck | |
| 5,325,850 A | 7/1994 | Ulrich et al. | |
| 5,325,851 A | 7/1994 | Reynolds et al. | |
| 5,333,606 A | 8/1994 | Schneider et al. | |
| 5,333,607 A | 8/1994 | Kee et al. | |
| 5,337,780 A | 8/1994 | Kee | |
| 5,343,857 A | 9/1994 | Schneider et al. | |
| 5,346,478 A | 9/1994 | Jinotti | |
| 5,348,542 A | 9/1994 | Ellis | |
| 5,349,950 A | 9/1994 | Ulrich et al. | |
| 5,354,267 A | 10/1994 | Niermann et al. | |
| 5,355,876 A | 10/1994 | Brodsky et al. | |
| 5,357,946 A | 10/1994 | Kee et al. | |
| 5,368,017 A | 11/1994 | Sorenson et al. | |
| 5,370,610 A | 12/1994 | Reynolds | |
| 5,385,560 A | 1/1995 | Wulf | |
| 5,445,141 A | 8/1995 | Kee et al. | |
| 5,449,348 A | 9/1995 | Dryden | |
| 5,460,613 A | 10/1995 | Ulrich et al. | |
| 5,487,381 A | 1/1996 | Jinotti | |
| 5,490,503 A | 2/1996 | Hollister | |
| 5,496,287 A | 3/1996 | Jinotti | |
| 5,513,627 A | 5/1996 | Flam | |
| 5,513,628 A | 5/1996 | Coles et al. | |
| 5,578,006 A | 11/1996 | Schön | |
| 5,582,161 A | 12/1996 | Kee | |
| 5,582,165 A | 12/1996 | Bryan et al. | |
| 5,598,840 A | 2/1997 | Lund et al. | |
| 5,605,149 A | 2/1997 | Warters | |
| 5,613,663 A | 3/1997 | Schmidt et al. | |
| 5,628,306 A | 5/1997 | Kee | |
| 5,642,726 A | 7/1997 | Owens et al. | |
| 5,664,594 A | 9/1997 | Kee | |
| 5,676,136 A | 10/1997 | Russo | |
| 5,715,815 A | 2/1998 | Lorenzen et al. | |
| 5,730,123 A | 3/1998 | Lorenzen et al. | |
| 5,735,271 A | 4/1998 | Lorenzen et al. | |
| 5,738,091 A * | 4/1998 | Kee et al. | 128/205.12 |
| 5,769,093 A | 6/1998 | Bays | |
| 5,769,702 A | 6/1998 | Hanson | |
| 5,775,325 A * | 7/1998 | Russo | 128/205.12 |
| 5,791,337 A * | 8/1998 | Coles et al. | 128/200.26 |
| 5,792,113 A | 8/1998 | Kramer et al. | |
| 5,813,402 A | 9/1998 | Jinotti | |
| 5,855,562 A | 1/1999 | Moore et al. | |
| 5,882,348 A | 3/1999 | Winterton et al. | |
| 5,919,174 A | 7/1999 | Hanson | |
| 6,165,168 A | 12/2000 | Russo | |
| 6,176,234 B1 * | 1/2001 | Salter et al. | 128/200.18 |
| 6,227,200 B1 * | 5/2001 | Crump et al. | 128/207.16 |

* cited by examiner

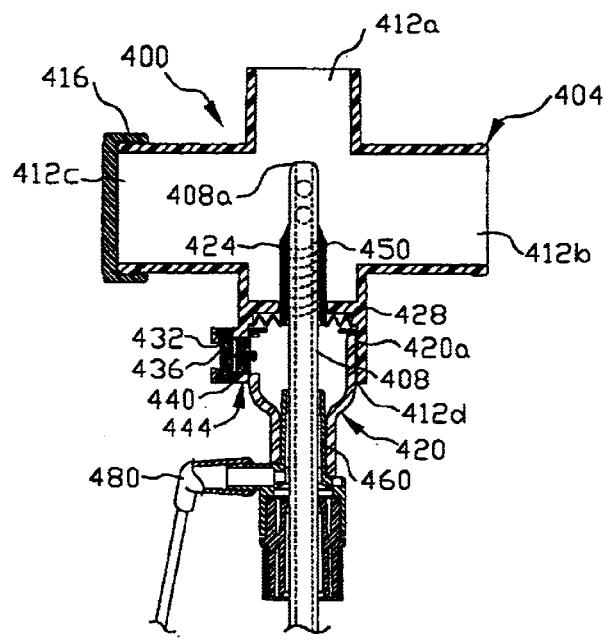
FIG 5A
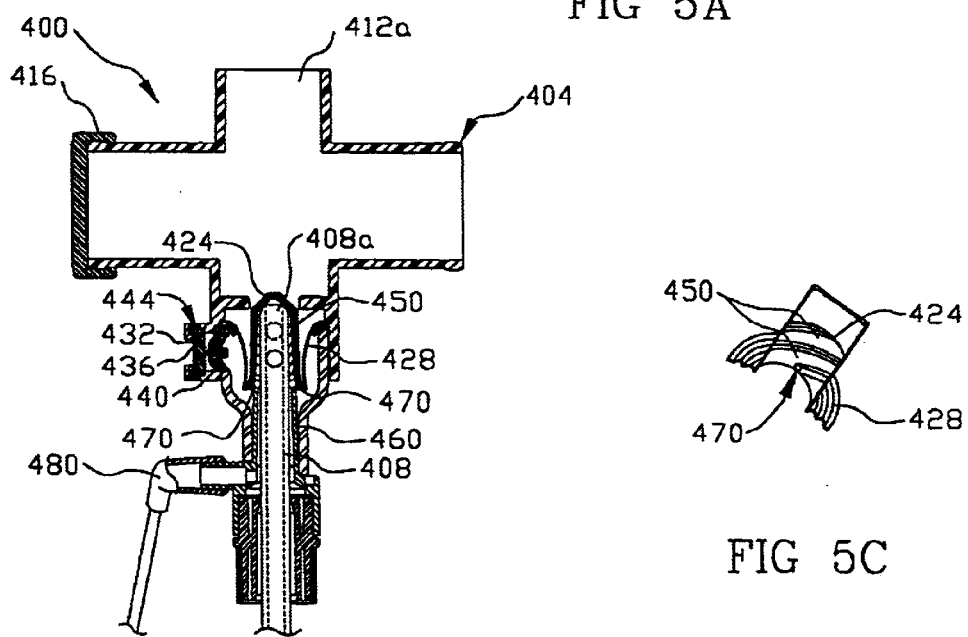
FIG 5B
FIG 5C

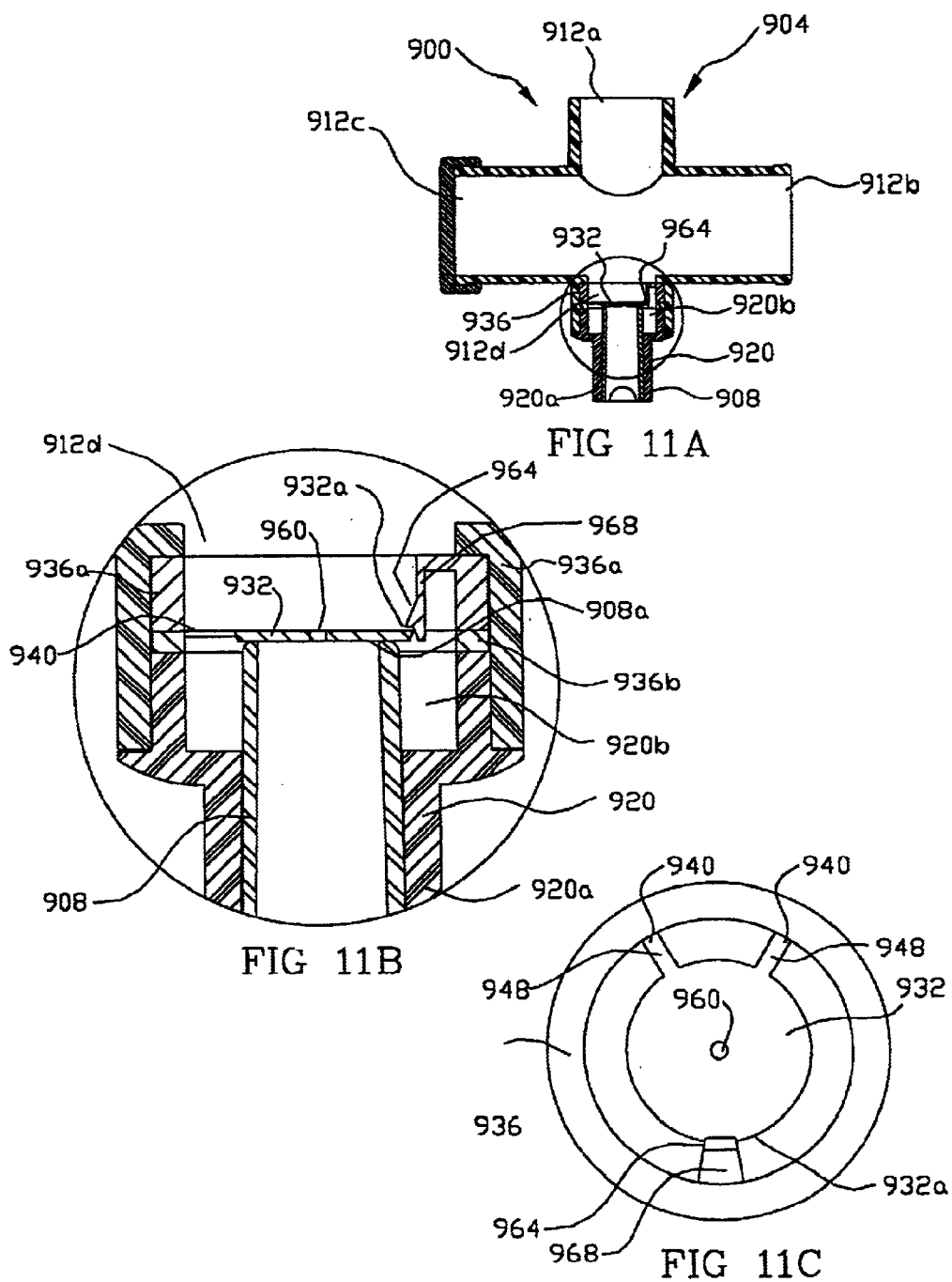

RESPIRATORY SUCTION CATHERER APPARATUS

RELATED APPLICATIONS

The present application is a continuation application of application Ser. No. 09/357,591 filed on Jul. 20, 1999, and now issued as U.S. Pat. No. 6,227,200 on May 8, 2002. application Ser. No. 09/357,591 is a Continuation-In-Part from application Ser. No. 09/157,605 filed on Sep. 21, 1998, now abandoned.

FIELD OF THE INVENTION

The present invention relates to a respiratory suction catheter system with an improved mechanism for cleaning the tip of the catheter without drawing an excessive amount of air from the respiration circuit to which the endotracheal catheter is attached. More specifically, the present invention relates principally to a closed suction endotracheal catheter system which provides improved cleaning of the catheter while minimizing or eliminating air drawn from the patient's ventilation circuit.

STATE OF THE ART

There are a variety of different circumstances under which a person may be required to have an artificial airway, such as an endotracheal tube, placed in his or her respiratory system. In some circumstances, such as surgery, the artificial airway's function is primarily to keep the patient's airway open so that adequate lung ventilation can be maintained during the procedure. In many other situations, however, the endotracheal tube will be left in the patient for a prolonged period of time. For example, with many patients, the endotracheal tube will remain in place to sustain mechanical ventilation for the life of the patient.

If an endotracheal tube is to be left in place for any substantial amount of time, it is critical that respiratory secretions be periodically removed. This is most often accomplished with the use of a respiratory suction catheter which is advanced into the endotracheal tube. As the suction catheter is withdrawn, a negative pressure is applied to the interior of the catheter to draw mucus and other secretions from the patient's respiratory system. While a substantial amount of the mucus and other secretions will be withdrawn through the catheter lumen, a portion of the mucus and other secretions remain on the outside of the catheter.

Because patient secretions can contain infectious agents, such as streptococcus, pseudomonus, staphylococcus and even HIV, it is important to shield clinicians from contact with the catheter. Likewise, it is important to shield patients' from communicable pathogens in the environment and those which may be carried by the clinician. This is particularly important because patients on mechanical ventilation often have compromised immune systems.

In addition to concerns of cross-contamination, suctioning a patients' artificial airway potentially interferes with proper respiration. The most common group of patients who have indwelling endotracheal tubes for prolonged periods are those who must be mechanically ventilated. Mechanically ventilated patients will typically have a fitting or manifold attached to the proximal end of the endotracheal tube (i.e., the end extending outside the patient) at an endotracheal tube hub. A pair of ventilator tubes extend from a mechanical ventilator and are typically attached to the manifold by an adapter. One tube provides inspiratory air to the patient for inhalation. The other tube allows for exhaled or expiratory air to exit the system.

Until the 1980s, it was common to disconnect the patient from the manifold and ventilator tubes each time the patient needed to be suctioned. Interference with the air supply to the patient, even if only for a few seconds, was often unnecessarily distressing to the patient. These problems were initially overcome in the invention disclosed in U.S. Pat. No. 3,991,762 to Radford. Radford developed what is commonly referred to as a closed suction catheter system. In a closed suction catheter system, a catheter is maintained within a protective sleeve which is attached to the manifold. When suctioning is desired, the catheter is advanced through the manifold and into the artificial airway. Negative pressure is then applied to the catheter and secretions within the patient's respiratory system are evacuated. Improvements were made to the system by the invention disclosed in U.S. Pat. No. 4,569,344 to Palmer. Palmer improved the system by reducing the risk of cross-contamination between the patient and the medical personnel using the device. Since that time, there has been a significant shift toward the use of closed suction catheter systems.

The advantage of closed suction catheters is that the ventilating circuit is not detached from the patient during suction procedures, as it is during open suction procedures. Because the catheter is reused a number of times over a twenty-four hour period, it is important that mucus and other secretions be cleaned from the catheter prior to periods of non-use. If the secretions are not removed, the risk of auto-contamination increases. It is also important to clean the lumen of the catheter to maintain suction efficiency.

There are several mechanisms by which the catheter may be cleaned. First, in U.S. Pat. No. 4,569,344, there is shown a lavage port which enables the user to inject liquid into the area surrounding the distal end of the catheter after it has been withdrawn from the patient. When liquid is injected into the closed suction catheter apparatus and suction is applied, the liquid helps to loosen and remove the secretions from the exterior of the catheter.

One significant problem with simply injecting liquid and applying suction to remove it, is that the suction also causes a volume of respiratory air to be removed through the catheter. In a "closed system", the air that is evacuated potentially disrupts the carefully controlled ventilatory cycles. Thus, the amount of respiratory air available to the patient is potentially decreased as a result of catheter cleaning. If the clinician has a hard time cleaning secretions from the catheter, suction may be applied through the catheter several times—thereby repeatedly drawing air from the ventilatory circuit.

Other closed suction catheters have been developed to have a cleaning or lavage chamber which is physically isolated from the ventilation circuit. For example, in U.S. Pat. No. 5,487,381 to Jinotti, there is shown a closed suction catheter which has a lavage chamber configured to receive the distal tip of the catheter as it is withdrawn from the manifold. A wall is then slid from an open position to a closed position to isolate the distal end of the catheter from the manifold and the ventilation circuit. A port is commonly provided to inject lavage solution into the cleaning chamber.

One problem which is present in such a configuration is that there is a lack of air flow to allow the suction catheter to clean properly. The application of negative pressure in the catheter can create a vacuum within the chamber in the absence of sufficient air flow into the chamber. Thus, isolating the chamber inhibits free evacuation of the cleaning solution. Additionally, movement of the wall requires an extra step on the part of the clinician.

Further, in one presently available product, the cleaning liquid commonly remains in the catheter due to the lack of airflow. Thus, contaminated liquids remaining in the catheter lumen can be reintroduced to the patient when the cleaning chamber is opened.

In addition to the above concerns, the closed suction catheters presently available suffer from the inability to clean the catheter tip to the most desirable extent. If pathogens or other contaminants remain on the catheter for too long, they can auto-contaminate the patient. Additionally if mucus and other secretions dry on the catheter, they can interfere with the suction efficiency, present an unsightly appearance and necessitate premature replacement of the closed suction catheter apparatus. Thus, there is a need for a catheter apparatus which has a mechanism for more effectively cleaning the distal end of the catheter without creating a substantial draw on respiratory air in the ventilation circuit.

SUMMARY OF THE INVENTION

It is an object of the present invention to provide an improved respiratory suction catheter apparatus which minimizes the amount of air drawn from the ventilation circuit during cleaning of the distal end of the catheter.

It is another object of the present invention to provide such a respiratory suction catheter apparatus which improves removal of mucus and other secretions from the distal tip of the catheter.

It is yet another object of the present invention to provide such a respiratory suction catheter apparatus wherein the mechanisms for improving cleaning function automatically to separate a cleaning area from the ventilation circuit.

It is still another object of the present invention to provide such a respiratory suction catheter apparatus which causes cleaning to be affected in a turbulent fluid flow.

It is a further object of the present invention to provide such a respiratory suction catheter apparatus which is easy to use and relatively inexpensive.

Various of the above and other objects of the invention are realized in specific illustrated embodiments of an improved respiratory suction catheter apparatus set forth more fully herein and claimed below. The embodiments of an improved respiratory suction catheter apparatus typically include a manifold for attachment to an artificial airway, such as an endotracheal tube, to form a ventilation circuit, a catheter which is displaceable through the manifold and into the artificial airway to suction secretions from the artificial airway and lungs, and a valve mechanism disposed adjacent the ventilation circuit to minimize the air drawn from the ventilation circuit of a patient while the catheter is being cleaned.

In accordance with one aspect of the invention, the valve mechanism is configured to automatically engage the catheter tip after it is withdrawn through the manifold to thereby minimize the amount of air drawn into the catheter during cleaning.

In accordance with another aspect of the present invention, the valve mechanism is configured to lock in a closed position when it is pulled toward the withdrawn catheter to thereby maintain isolation between the catheter tip and the airway through the manifold.

In accordance with another aspect of the present invention, the valve mechanism is provided with an air makeup to allow makeup air into the catheter and thereby ensure proper evacuation of secretions and any liquid used to clean the catheter.

In accordance with another aspect of the present invention, an air turbulence enhancing mechanism is provided for increasing turbulent airflow around the distal end of the catheter to thereby improve removal of secretions from the catheter.

In accordance with still another aspect of the present invention, an air makeup mechanism is disposed so as to provide makeup air to the distal end of the catheter which is not drawn from the ventilation circuit.

In accordance with still yet another aspect of the present invention, a pair of wiper seals are used to more effectively clean the distal end of the catheter tube.

BRIEF DESCRIPTION OF THE DRAWINGS

The above and other objects, features and advantages of the invention will become apparent from a consideration of the following detailed description presented in connection with the accompanying drawings in which:

FIG. 4C shows a fragmented, cross-sectional view of the embodiment of FIGS. 4A and 4B, with an air makeup mechanism in an open position to facilitate suctioning of mucus and the like;

FIG. 5A shows a fragmented, cross-sectional view of an alternative embodiment of an improved respiratory suction catheter apparatus having a valve in an open position in accordance with the principles of the present invention;

FIG. 5B shows a fragmented, cross-sectional view of the embodiment shown in FIG. 5A with the valve in a closed position;

FIG. 5C shows a partial cross-sectional view of the valve of the embodiment shown in FIGS. 5A and 5B;

FIG. 11A shows a fragmented, cross-sectional view of another embodiment of an improved endotracheal catheter which has a locking valve mechanism disposed thereon;

FIG. 11B shows a close-up view of the locking valve mechanism and associated structure of FIG. 11A;

FIG. 11C shows a close-up end view of the locking valve mechanism of FIGS. 11A and 11B;

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims. Those skilled in the art will appreciate that aspects of the various embodiments discussed may be interchanged and modified without departing from the scope and spirit of the invention.

Figure 1:
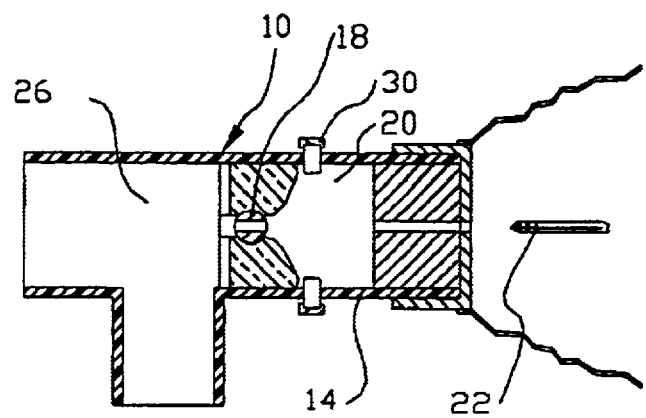
FIG. 1 shows a cross-sectional view of a manifold and catheter cleansing mechanism in accordance with the teachings of the prior art.

Referring to FIG. 1, there is shown a cross-sectional view of a manifold 10 and catheter cleansing mechanism 14 in accordance with the teachings of the prior art. The manifold has a valve mechanism in the form of a rotatable rod 18 for selectively isolating a lavage chamber 20 from the ventilation circuit 26. When the distal end of the catheter 22 is disposed in the lavage chamber 20, a lavage solution can be injected through a side port 30 to help wash the mucus and other secretions from the exterior of the catheter 22. Because of the relative size and dimensions of the lavage chamber 20, however, there is nothing to force vigorous interaction between the lavage solution and the secretions on the exterior of the catheter. Additionally, because the lavage chamber is not configured for makeup air to enter when the rotatable rod 18 is closed, a vacuum can be created in the lavage chamber 20 which interferes with effective suctioning.

An additional disadvantage of the embodiment shown in FIG. 1 is that the closure mechanism for such devices typically must be manually activated. If the user fails to close the rotatable rod 18, actuation of suction through the catheter will draw air from the ventilation circuit 26.

Figure 2:
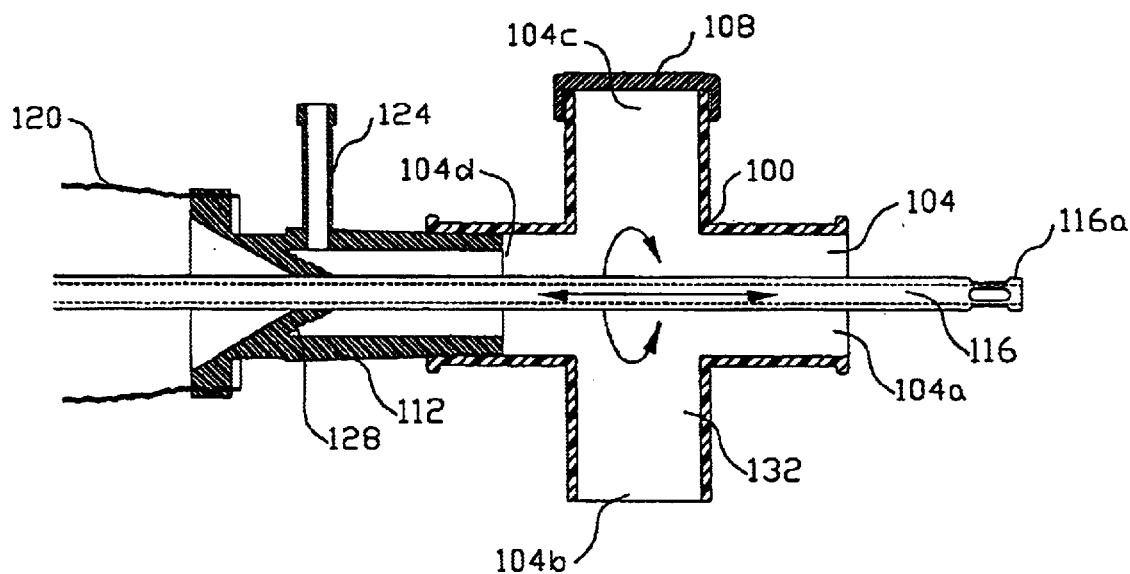
FIG. 2 shows a cross-sectional view of a manifold and catheter cleaning mechanism in accordance with the teachings of another embodiment of the prior art.

Turning now to FIG. 2, there is shown a cross-sectional view of an alternative embodiment of the prior art. The manifold 100 is provided with a plurality of ports 104. A first port 104a is attached to the hub of an endotracheal tube of the patient to conduct respiratory air to and from the endotracheal tube. Thus the manifold forms part of a ventilation circuit. The air is typically provided to and removed from the manifold through a second port 104b which is attached to a pair of ventilation tubes via a connector (not shown). The ventilation tubes are, in turn, connected to a mechanical ventilator ( not shown) in a manner which will be well known to those skilled in the art.

A third port 104c is provided opposite the second port 104b. The third port 104c is typically covered with a cap 108 which is removed when "blow-by" is desired to wean a patient from forced ventilation.

The manifold also has a fourth port 104d. A coupling 112 is configured to form a force-fit engagement with the fourth port 104d and effectively connects the catheter 116 and a protective sleeve 120 to the manifold 100. Disposed adjacent a proximal end of the coupling 112 is a lavage port 124 through which a cleaning liquid can be injected to rinse the exterior of the catheter 116. Such a configuration is advantageous because the lavage port 124 is positioned adjacent a seal 128 which is configured to wipe mucus and other secretions from the catheter 116 as is drawn through the seal. Thus, a user will typically withdraw the catheter 116 until the distal end 116athereof is positioned slightly distally of the seal 128, and then the cleaning solution will be injected into the lavage port 124 to assist in the removal of secretions. While such a method of removing the secretions is generally effective, it can draw more air from the ventilation circuit 132 than is necessary to effectively clean the distal end 116a of the catheter 116. Additionally, it is common for respiratory therapists and other clinicians to maintain the suction on as the distal end 116a of the catheter 116 is drawn from the first port 104a to a position immediately adjacent the seal 128.

Figure 3A:
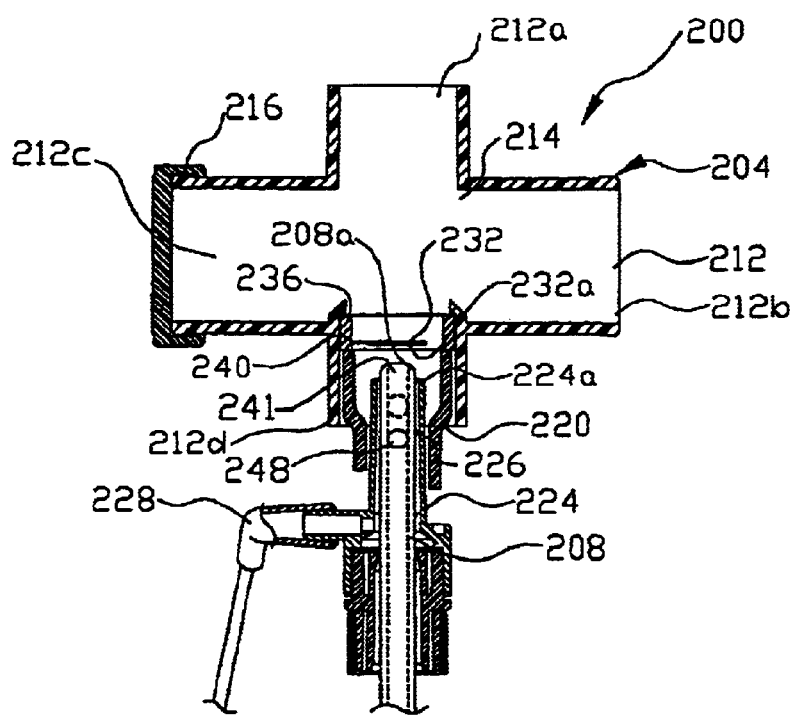
FIG. 3A shows a cross-sectional view of the manifold and distal portion of a catheter of an improved respiratory suction catheter apparatus with a valve member in an open position in accordance with the principles of the present invention.

Turning now to FIG. 3A, there is shown a cross-sectional view of a portion of an improved endotracheal catheter, generally indicated at 200. The endotracheal catheter includes a manifold, generally indicated at 204 and a catheter 208. The manifold 204 includes a plurality of ports 212a–c. A first port 212a is configured for attachment to the proximal end of an artificial airway, such as the hub of an endotracheal tube, tracheostomy tube, etc. A second port 212b is typically connected to a pair of ventilator tubes (not shown) by means of an adaptor (not shown), in accordance with common practice in the art.

As used herein, distal refers generally to the direction of the patient, while proximal refers to the direction of the user. Unless otherwise noted, the drawings of FIG. 2A are oriented such that the distal (patient) end is toward the top of the page, while the proximal (user) end is toward the bottom of the page.

During normal usage, conditioned inspiratory air is forced through one of the ventilator tubes, through the second port 212b and the first port 212a and into the patient's lungs via the artificial airway. Exhaled air is carried through the first port 212a and then the second port 212b and out through the other ventilator tube. Thus, the manifold 204 forms part of a ventilation circuit 214 through which respiratory air is cycled.

Also forming part of the manifold 204 is a third port 212c. The third port 212c is typically covered by a cap 216. Whenever mechanical ventilation is used, it is the goal to someday return the patient to voluntary or spontaneous breathing. To accomplish this, the patient must usually be weaned from the mechanical ventilation—to spontaneous breathing. To this end, the cap 216 may be removed from the third port 212c so that oxygenated air is passed by the patient's endotracheal tube, but inspiratory air is not forced into the patient's lungs by means of a totally closed circuit. This situation, commonly called "blow-by," enables the patient to gradually resume natural or spontaneous breathing.

The manifold 204 also has a fourth port 212d. The fourth port 212d is disposed generally opposite the first port 212a and is configured to allow the catheter 208 to slide therethrough and into the first port to enable suctioning of the patient. At the completion of suctioning, the catheter 208 is pulled back into the fourth port 212d to prevent interference with the ventilation circuit 214.

Disposed between the wall forming the fourth port 212d and the catheter 208 is a coupling or adapter 220. On an outer extreme, the adapter 220 engages the wall defining the fourth port 212d. On an inner extreme, the adapter 220 engages a collar 224 which closely surrounds the catheter 208 so as to leave a small cylindrical space 226 around the catheter 208. Ideally the space between the catheter 208 and the collar 224 is between 0.005 and 0.015 inch. This proximity provides two important advantages. First, if lavage needs to be provided to the lungs of the patient, injecting lavage solution through the lavage port 228 and into the cylindrical space 226 causes a stream of lavage solution to be directed out the distal end 224a of the collar and through the first port 212a. If the spacing between the catheter 208 and the collar 224 is too large (as in the art discussed above), the lavage solution cannot be thus directed. Second, as the catheter 208 is drawn back into the collar 224 after use, the collar helps to wipe any heavy layers of mucus or other secretions from the outside of the catheter.

Injecting lavage/cleaning solution through the lavage port 228 further removes the secretions from the exterior of the catheter 208 and enhances evacuation by suction in the catheter. This configuration also minimizes the volumes of air and cleaning solution necessary to effect cleaning.

While the collar 224 configuration shown in FIG. 3A is beneficial, it is still common to have secretions build up on the distal end 208a of the catheter 208. If such build up is not promptly removed, it can interfere with the ability of the catheter to properly suction the patient. It can also serve as a culture medium for pathogens within the closed suction catheter system.

In accordance with one of the principles of the present invention, it has been found that selective obstruction of the airflow into the distal end 208a of the catheter 208 significantly improves catheter cleaning. Additionally, it has been found that such a mechanism for improved cleaning also minimizes the withdrawal or air from the ventilation circuit 214.

As shown in FIG. 3A, a flap 232 is hingedly attached to an annular ring 236 disposed inside the fourth port 212d so as to enable the flap 232 to pivot with respect to the ring to form a self-closing valve member. Of course, the flap 232 could be attached directly to the wall of the manifold 204 defining the fourth port 212d or to the adapter 220. The hinged attachment 240 allows the flap 232 to selectively move while maintaining alignment with the catheter tip, thereby creating a self-closing flap valve.

Figure 3B:
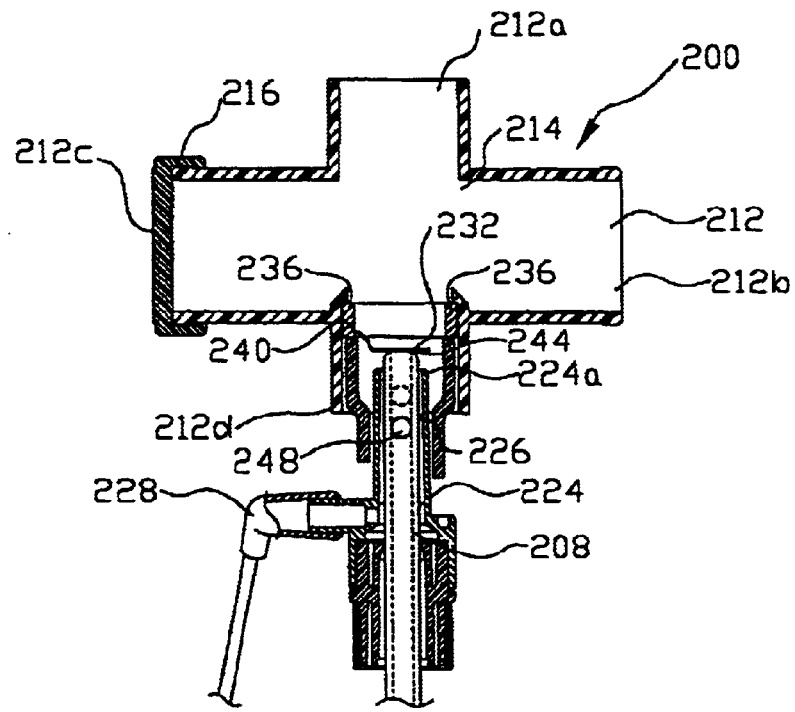
FIG. 3B shows a cross-sectional view of the manifold and catheter portion shown in FIG. 3A, with the valve in a second, closed position.

As shown in FIG. 3B, the flap 232 is positioned to align with the distal end 208a of the catheter 208 when the catheter is almost completely withdrawn into the collar 224. The hinged attachment 240 is sufficiently flexible that suction through the distal end 208a of the catheter 208 will draw the flap 232 proximally from a first, distal position into a second, proximal position, wherein the flap contacts with the distal end of the catheter. Thus, with the flap 232 and related structures form a self-closing valve wherein no additional external manipulation of the catheter system is needed to close the valve.

As with most closed suction catheters, the catheter 208 includes a primary aperture 244 in the distal end 208a and one or more lateral apertures 248 positioned slightly proximal from the distal end.

When the flap 232 moves proximally and contacts the distal end 208a of the catheter 208, suction through catheter tip aperture 244 is dramatically reduced or eliminated. Decrease in suction flow through the aperture 244 causes increased suction flow in the lateral apertures 248, thereby increasing the ability of the lateral apertures to evacuate any secretions contained between the outside of the catheter 208 and the interior of the collar 224. Because the lateral apertures 248 are generally smaller than the distal aperture 244 and because airflow to the lateral apertures is limited by the collar 224, a substantial decrease in the amount of air drawn from the ventilation circuit is achieved while simultaneously improving cleaning of the catheter 208.

As shown in FIGS. 3A and 3B, the proximal side 232a (i.e., the side opposite the ventilation circuit 214) of the flap 232 is generally planar. In such a configuration, the proximal side 232a of the flap 232 will typically form a substantially complete seal with the distal end 208a of the catheter 208.

Figure 3C:
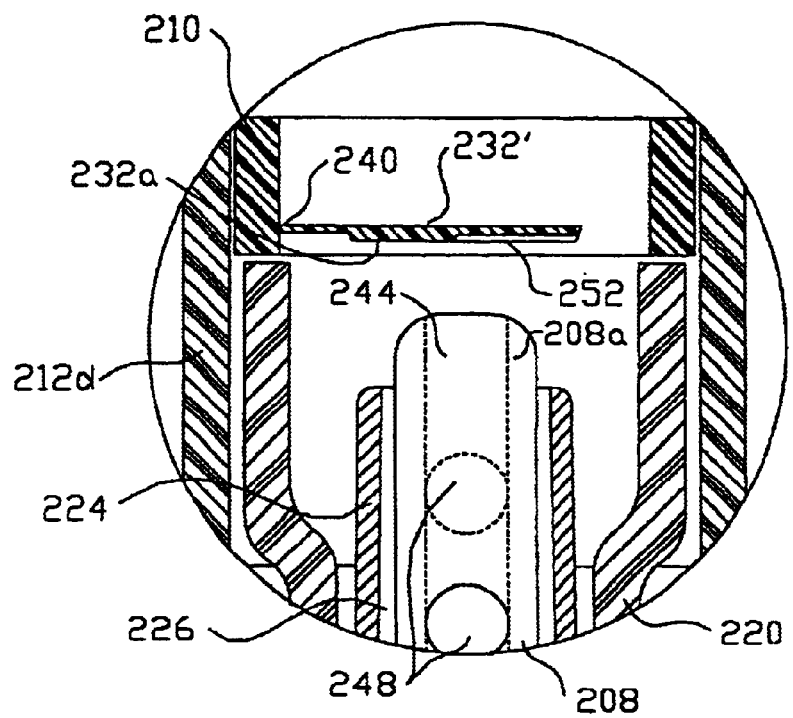
FIG. 3C shows a fragmented, close-up cross-sectional view of one embodiment of the improved respiratory suction catheter apparatus shown in FIG. 3A.

Turning now to FIG. 3C, there is shown a close-up cross-sectional view of the embodiment shown in FIGS. 3A and 3B with a slight modification to the flap 232. Unlike the flap 232 in FIGS. 3A and 3B which is substantially planar, the flap 232' in FIG. 3C has a channel 252 formed therein on the proximal side 232a. The channel 252 prevents the flap 232' from forming an airtight engagement with the distal end 208a of the catheter 208. In other words, the channel 252 ensures that a measured volume of air will be drawn into the aperture 244 at the distal most end 208 of the catheter.

The measured volume of air which is drawn in through the channel 252 can have an important effect. Specifically, the air creates turbulent airflow both within the catheter 208 and immediately around its exterior. The turbulent airflow in turn, assists in breaking up agglomerations of mucus and secretions which lavage/cleaning solution alone may not. Thus, the turbulent airflow helps to provide improved cleaning of the distal end 208a of the catheter 208. This is in sharp contrast to many of the prior art devices which have advocated the use of a lavage/cleaning chamber to clean the exterior of the catheter. Because the lavage/cleaning chamber is usually substantially larger than the catheter or because makeup air is not specifically provided, it is difficult to create turbulent airflow within the chamber. Without turbulent airflow, the mucus and other secretions are often not removed from the exterior of the catheter.

Figure 3D:
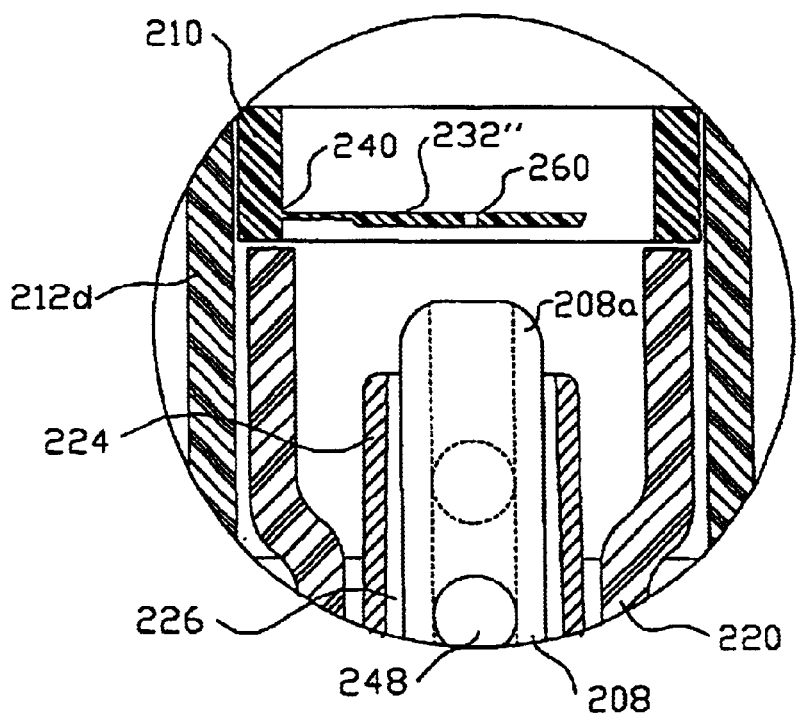
FIG. 3D shows a fragmented, close-up cross-sectional view of another embodiment of the improved respiratory suction catheter apparatus shown in FIG. 3A.

Turning now to FIG. 3D, there is shown yet another variation of the flap 232 shown in FIGS. 3A and 3B. Rather than having a channel formed in a proximal side thereof, the flap 232" has an aperture 260 formed therein so as to allow a relatively small amount of air to pass through the flap 232". As with the embodiment of FIG. 3O, the small hole creates turbulent airflow at the distal end 208a of the catheter 208 and thereby improves cleaning. It is currently believed that an aperture 260 in the flap 232" with a diameter of about 0.03 inches is preferred.

Figure 3E:
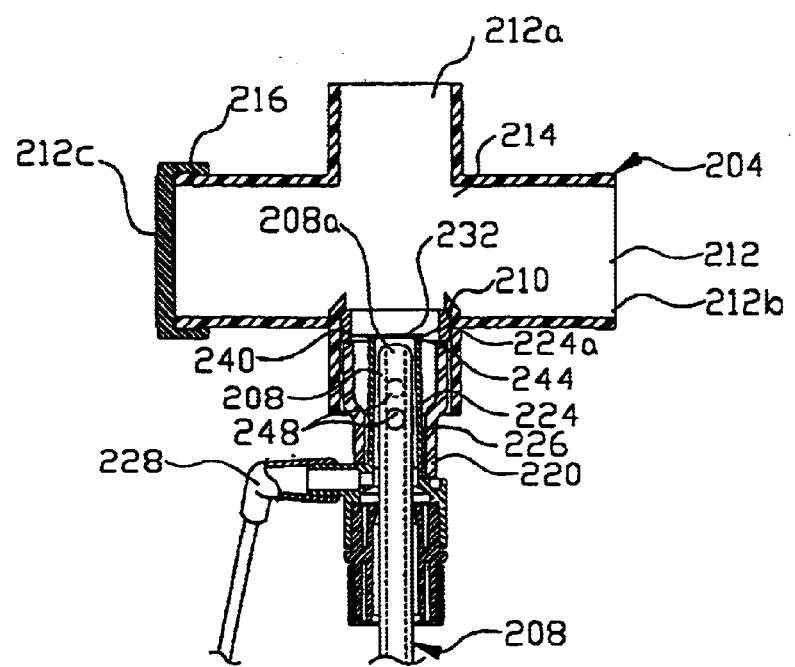
FIG. 3E shows a cross-sectional view similar to those shown in FIGS. 3A through 3D of an alternate embodiment wherein the flap engages the collar.

While shown in FIGS. 3A through 3D as engaging the distal end 208a of the catheter 208, the flap 232 forming a flap valve need not engage the catheter itself. Thus, for example, FIG. 3E shows an embodiment similar to those shown in FIGS. 3A through 3D, except that the flap 232 is disposed to engage the distal end 224a of the collar 224 rather than the distal end 208a of the catheter 208. In such a configuration, suction flow can still be achieved through the aperture 244 at the distal end 208a of the catheter 208.

Preferably, a source of makeup air will be provided. This can be accomplished by using either of the flap configurations shown in FIGS. 3C and 3D. In the alternative, a small hole can be formed in the collar 224 to facilitate a small amount of makeup air being present to enhance suction flow and to increase turbulence.

Regardless of which configuration of those shown in FIGS. 3A through 3E is used, the result is an improved ability to clean the distal end 208a of the catheter 208, while at the same time significantly reducing the amount of air which is withdrawn from the ventilation circuit 214. Thus, consistent ventilation is provided to the patient, and the clinician is able to more easily clean the catheter 208.

Figure 4A:
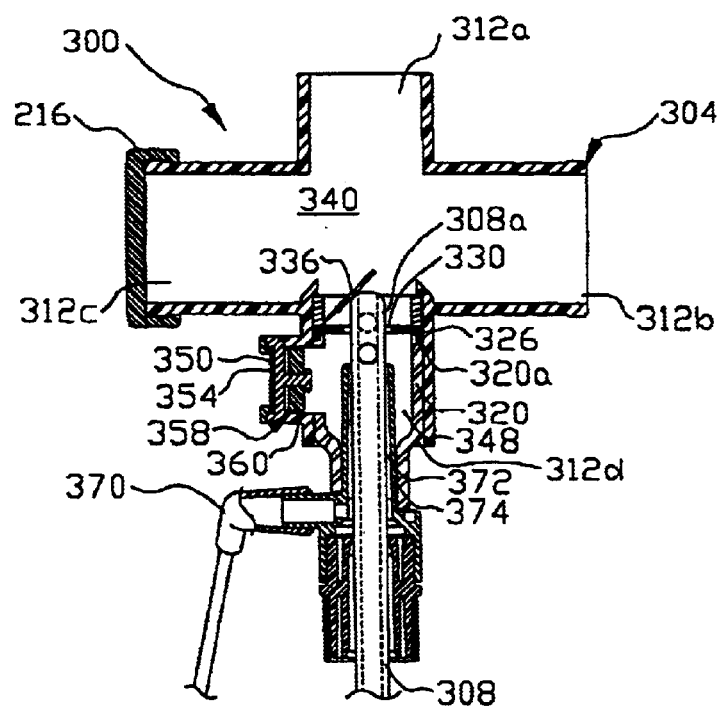
FIG. 4A shows a fragmented, cross-sectional view of an alternative embodiment of an improved respiratory suction catheter apparatus having a valve in an open position in accordance with the principles of the present invention.

Turning now to FIG. 4A, there is shown another embodiment of an improved respiratory suction catheter apparatus, generally indicated at 300, made in accordance with the principles of the present invention. The improved respiratory suction catheter apparatus 300 includes a manifold 304 and a catheter 308. As with the previous embodiment, the manifold 304 includes a first port 312a, a second port 312b, a third port 312c and a fourth port 312d.

An adapter 320 is disposed in the fourth port 312d in such a manner as to make the manifold 304 and the catheter 308 a functionally integrated unit. The adapter 320 may be adhesively attached to the manifold 304, or may be simply force-fit.

Unlike the embodiment discussed with FIGS. 3A through 3D, an annular ring is not disposed in the manifold 304 independent of the adapter 320. Rather, an annular ring 326 extends inwardly from a distal end 320a of the adapter 320. The annular ring 326 defines an aperture or opening 330 through which the catheter 308 can be extended. Thus, the opening 330 is slightly larger than the exterior of the catheter 308.

Also extending inwardly from the adapter 320 is a flap 336. The flap 336 is preferably hingedly attached to either the adapter directly or to the annular ring 326. When no suction is applied to the catheter 308, or when the distal end 308a of the catheter is disposed distally from the flap 336, the flap will generally extend distally from the annular ring 326 and provide virtually no resistance to advancement of the catheter 308.

Figure 4B:
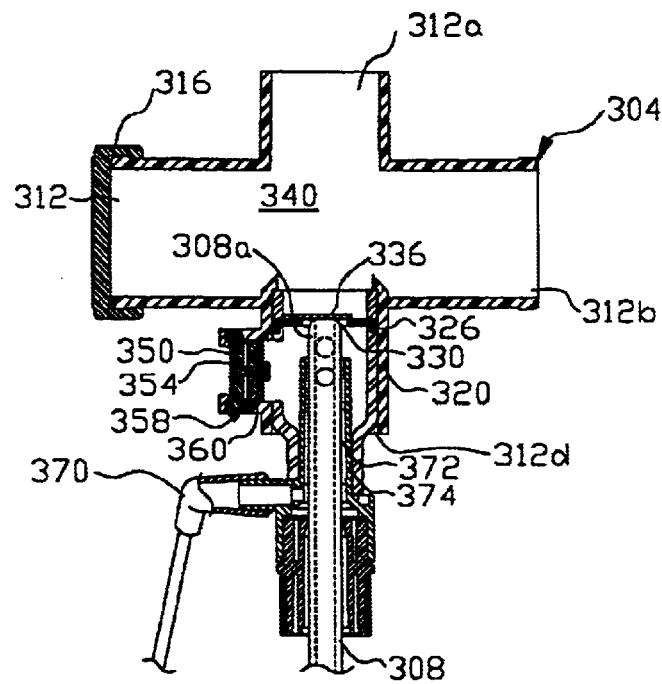
FIG. 4B shows a fragmented, cross-sectional view of the embodiment of FIG. 4A, wherein the valve is in a closed position to isolate the catheter from the ventilation circuit.

As shown in FIG. 4B, as the distal end 308a of the catheter 308 is withdrawn through the annular ring 326 while suction is applied, a vacuum is created which pulls the flap 336 over the opening 330, thereby isolating the distal end 308a of the catheter 308 from the ventilation circuit 340 and preventing the catheter from drawing air away from a patient to whom the manifold is attached. While the flap 336 could be configured in the manner shown in FIGS. 3C and 3D, the present configuration does not necessitate the use of makeup air from the ventilation circuit 340.

If the catheter 308 were simply left in the chamber 348 behind the flap 336/annular ring 326 and lavage were injected into the chamber, a substantial negative pressure could build within the chamber. Additionally, because no relief is provided, it would be difficult to suction mucus etc. from the chamber once the lavage source had been sucked dry. To overcome these problems with the prior art, the embodiment in FIGS. 4A through 4C has a makeup air inlet, generally indicated at 350 which is formed in a portion of the wall defining the fourth port 312d of the manifold and the adapter 320. The makeup air inlet 350 preferably includes a filter 354 which is selected to substantially prevent cross-contamination between the environment/clinicians and the patient. Disposed adjacent to the filter material is a flexible barrier 358 which forms a one-way valve 360.

Figure 4C:
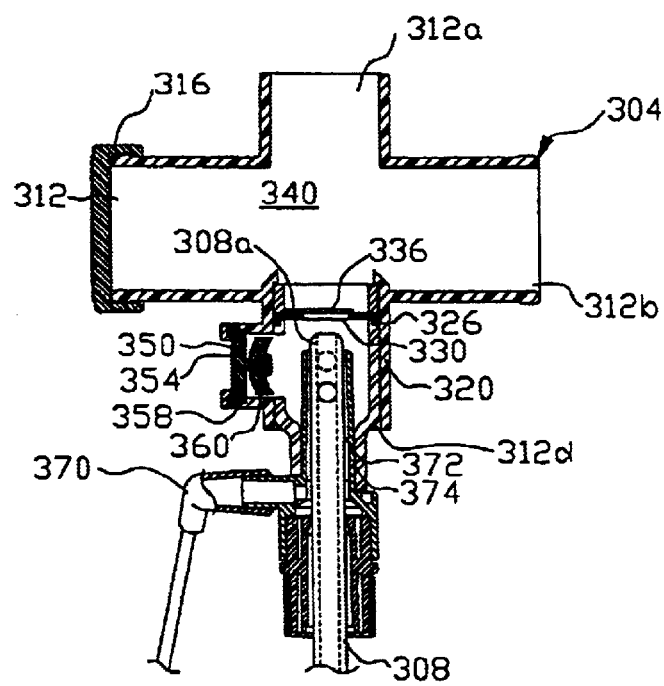

As shown in FIGS. 4B and 4C, the one-way valve 360 will generally be closed when the catheter 308 is in an extended position, wherein the catheter extends through the opening 330 in the annular ring 326. However, once the distal end 308a of the catheter 308 has been withdrawn through the opening 330 in the annular ring 326 and the flap 336 has been drawn closed, a vacuum will quickly develop on the side of the flap 336 opposite the ventilation circuit 340. The vacuum causes the one-way valve 360 to open and allow a supply of makeup air to enter the chamber. The makeup air flowing past the flexible one-way valve member 360 helps to create turbulent airflow and facilitate removal of any respiratory secretions on the catheter 308. This is preferably accomplished at about the same time the user utilizes the lavage port 370 to inject lavage/cleaning solution through the space 372 between the collar 374 and the catheter 308. It will be appreciated that the one-way valve 360 could be configured to provide very little resistance to air inflow, or could be configured to require a substantial vacuum to be present before makeup air is allowed into the area proximal the flap 336.

Turning now to FIG. 5A, there is shown a fragmented, cross-sectional view of an alternative embodiment of an improved respiratory suction catheter apparatus, generally indicated at 400. The respiratory suction catheter apparatus includes a manifold 404 and a catheter 408 which is moveable through the manifold to suction secretions from a patient's lungs. As with the previously discussed embodiments, the manifold includes a first port 412a for attachment to an endotracheal tube or other artificial airway, a second port 412b for attachment to the ventilator tubes of a mechanical ventilator, a third port 412c which is covered with a cap 416, and a fourth port 412d which receives the connector or adaptor 420.

Disposed at the distal end 420a of the adaptor 420 is a valve 424 in a configuration which is commonly referred to as a duckbill valve. The valve 424 is formed by a piece of resilient material which opens as the catheter 408 is advanced therethrough, and closes when the catheter is withdrawn. The valve 424 is attached to the adaptor 420 by a flexible base 428.

Also disposed in the adaptor 420 is an air inlet 432 which includes a filter material 436 and a resilient member 440 configured to form a one-way valve 444 similar to that discussed in the previous embodiment. While duckbill valves have been used in endotracheal catheter systems in the past, the valve 424 shown in FIGS. 5A through 5C is substantially advanced in several respects. First, as shown in FIGS. 5A and 5C, the interior of the valve 424 has helical grooves 450 formed therein. The helical grooves 450 help to create turbulent airflow around the distal end 408a of the catheter 408. Additionally, the flexible base 428 is configured to allow the adaptor 420 to be drawn toward the collar 460 to thereby reduce space and improve removal of secretions from the exterior of the catheter 408.

Turning now specifically to FIG. 5B, there is shown a cross-sectional view similar to that shown in FIG. 5A, but with the distal end 408a of the catheter 408 in a retracted position. Once the distal end 408a of the catheter 408 is withdrawn proximally from the valve 424, the suction through the catheter works against the flexible base 428 of the valve and draws the valve toward the collar 460. A pair of air inlets 470 are disposed at the base 428 of the valve 424 and allow air into the valve.

Applying suction to the valve 424 and through the air inlets 470 as shown in FIG. 5B creates a vacuum between the adaptor 420 and the flexible base 428, thereby causing the one-way valve 444 to open and allow air into the air inlets 470 at the top of the collar 460. This air mixes with the water injected through the lavage port 480 and turbulently travels along the distal end 408a of the catheter 408. The turbulent motion of the air/water mixture is enhanced by the helical grooves 450.

Once suction through the catheter 408 is stopped, there is no longer a negative pressure from the catheter to keep the one-way flap valve 444 closed, or to maintain the valve 444 adjacent to the distal end of the collar. Thus, the valve 424 may return to the position shown in FIG. 5A, except that it will be closed as the catheter 408 remains substantially in the collar until the next use.

Figure 6A:
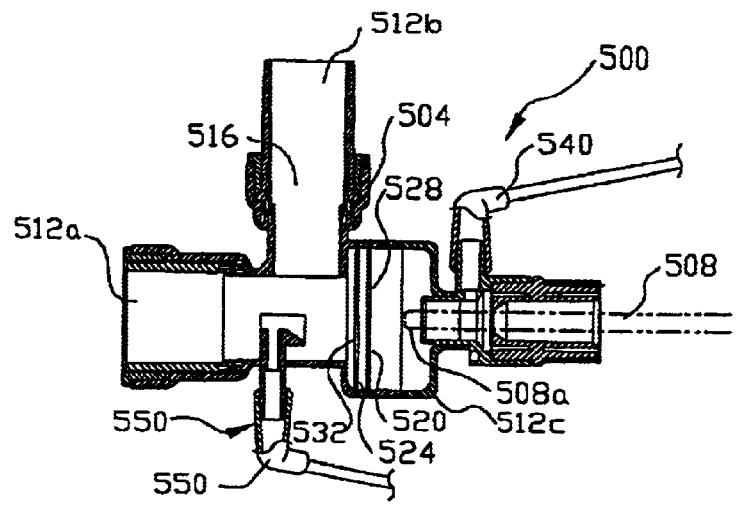
FIG. 6A shows a fragmented, cross-sectional view of yet another alternative embodiment of an improved respiratory suction catheter apparatus made in accordance with the principles of the present invention.

Turning now to FIG. 6A, there is shown a cross-sectional view of yet another alternative embodiment of an improved endotracheal catheter made in accordance with the principles of the present invention. The endotracheal catheter 500 includes a manifold 504 and a catheter 508. The manifold 504 has a first port 512a for attachment to the hub of an artificial airway of a patient, and a second port 512b for attachment to the ventilator tubes (not shown) of a mechanical ventilator so as to define a ventilation circuit 516.

Figure 6B:
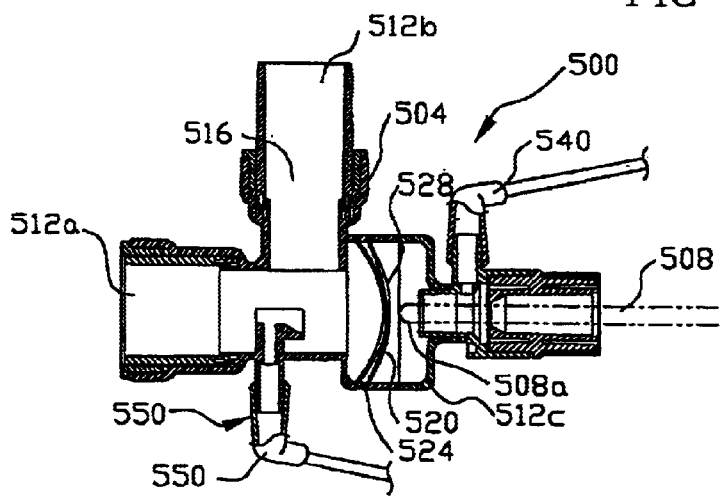
FIG. 6B shows a fragmented, cross-sectional view of the embodiment shown in FIG. 6A in a closed configuration.
Figure 6C:
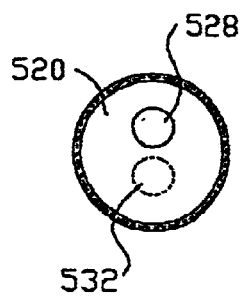
FIGS. 6C and 6D show end views of the valve mechanism of the embodiment shown in FIGS. 6A and 6B in a relaxed position and with a catheter extending therethrough, respectively.
Figure 6D:
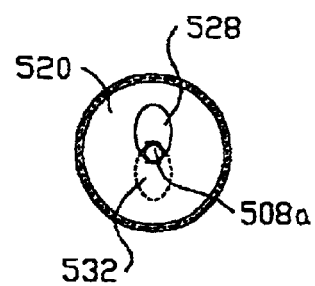

The manifold also includes a third port 512c which is configured to receive the catheter 508. Disposed in the third port 512c are a pair of floating flexible disks or membranes 520 and 524. Each of the disks defines an aperture or opening 528 and 532, respectively, through which the catheter 508 may be slid. An end view of the disks 520 and 524 with the catheter being slid therethrough is shown in FIG. 6D.

When the catheter 508 is withdrawn through the openings 528 and 532 in the disks, a vacuum is created proximally of the disks 520 and 524. The vacuum draws both of the disks toward the end of the catheter 508, as shown in FIG. 6B. This substantially seals the two disks together in an arrangement without overlapping openings as shown in FIGS. 6B and 6C. This configuration minimizes or eliminates (depending on the seal) air flow out of the ventilation circuit as lavage solution is injected through the lavage port 540 and the distal end 508a of the catheter 508 is cleaned.

Because the lavage port 540 is disposed behind the disks 520 and 524 which provide a significant impediment to lavage flowing to the lungs if needed, a second lavage port 550 can be added distally from the disks. The second lavage port 550 typically would not be used for cleaning of the catheter 508.

Figure 7A:
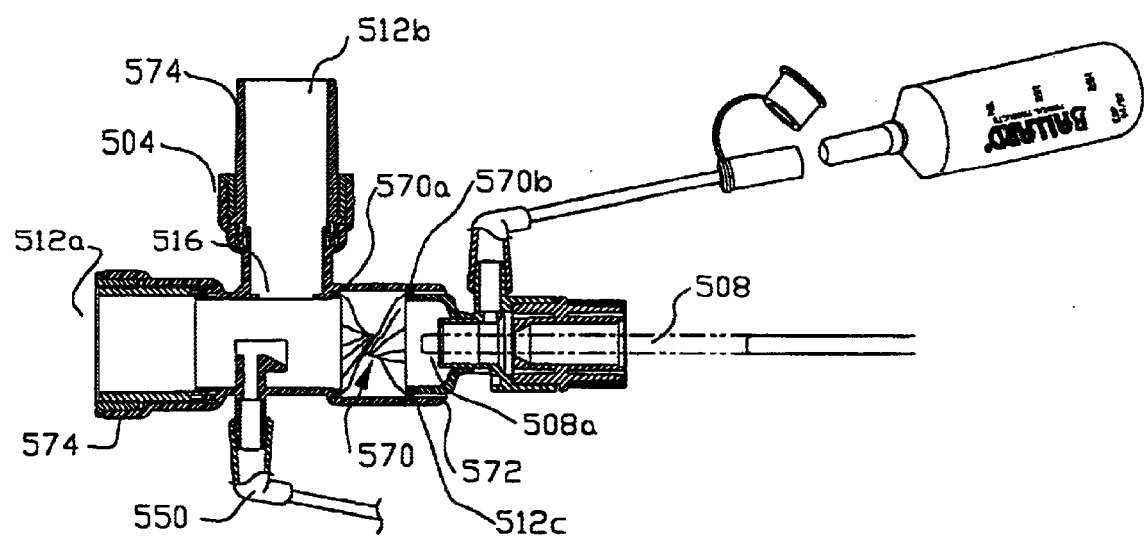
FIG. 7A shows a fragmented, cross-sectional view of still another embodiment of an improved respiratory suction catheter apparatus made in accordance with the principles of the present invention.

Turning now to FIG. 7A there is shown a cross-sectional view of still another embodiment of an improved endotracheal catheter made in accordance with the principles of the present invention. Most portions of the endotracheal catheter shown in FIG. 7A are the same as those discussed with respect to FIGS. 6A through 6D and are numbered accordingly. The one major difference between the embodiments of FIGS. 6A through 6D and FIG. 7A is that the disks 520 and 524 of the previous embodiment are replaced with a resilient closing membrane 570 which is attached at one end 570a to the manifold 504 and at an opposing end 570b to an adapter 572 holding the catheter 508. The adapter 572 or manifold 504 can be rotated to twist the membrane 570 and thereby either reduce or enlarge the size of a hole 580 (FIG. 7B) formed by the material. By twisting the resilient material 570 to close the hole 580, the drawing of air from the ventilation circuit 516 can be reduced or even eliminated.

When suctioning of a patient is desired, the resilient material 570 is rotated to allow the catheter to pass therethrough. Because swivels 574 are disposed on the first and second ports 512a and 512b, the rotation of the resilient material to expand or contract the hole therethrough will provide virtually no discomfort to the patient, while effectively controlling the amount of air which is drawn from the ventilation circuit 516 when the distal end 508a of the catheter 508 is being cleaned.

Figure 7B:
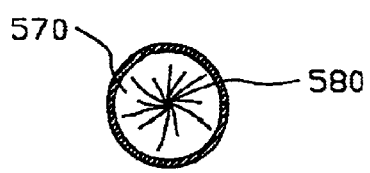
FIG. 7B shows a partial end view of the improved respiratory suction catheter apparatus of FIG. 7A in a closed position.

FIG. 7B shows an end view of the resilient membrane 570. By rotating the resilient membrane 570 in one direction, the hole 580 is enlarged. By rotating the resilient material in an opposing direction, the size of the hole 580 is reduced.

Figure 8A:
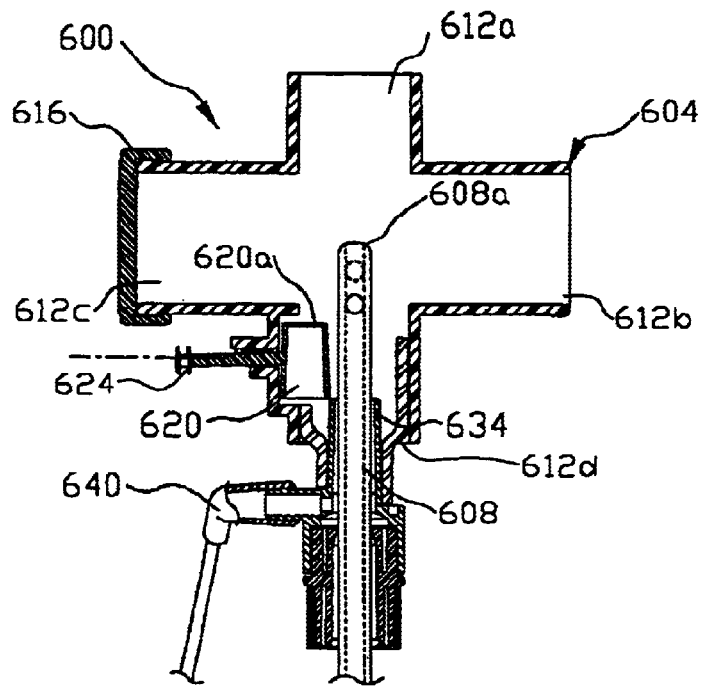
FIG. 8A shows a fragmented, cross-sectional view of still yet another embodiment of an improved respiratory suction catheter apparatus made in accordance with the principles of the present invention.
Figure 8B:
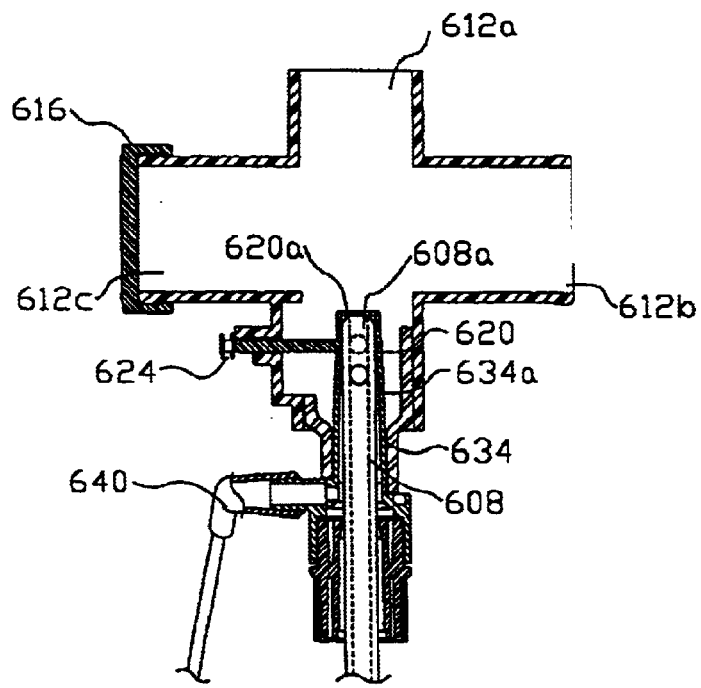
FIG. 8B shows a fragmented, cross-section view of the improved endotracheal catheter of FIG. 8A, wherein the valve mechanism is in a closed configuration.

Turning now to FIGS. 8A and 8B, there is shown yet another endotracheal catheter embodying principles of the present invention. The respiratory suction catheter apparatus 600 includes a manifold 604 and a catheter 608 which is moveable through the manifold. As with many of the embodiments discussed previously, the manifold 604 includes a first port 612*a* for connection to the hub of an endotracheal tube, a second port 612*b* for connection (via ventilator tubes) to a mechanical ventilator, and a third port 612*c* and cap 616 which can be used for blow-by.

The fourth port 612*d* is different from those discussed previously because it has a shroud 620 placed therein. The shroud 620 is attached to a plunger 624 so as to allow the user to move the shroud between a first position adjacent the sidewall of the fourth port 612*d* (FIG. 8A) and a second position (FIG. 8B) wherein the shroud is disposed approximately at the center of port 612*d*.

During use of the respiratory suction catheter apparatus 600, the shroud 620 will typically be moved into the first position so that it does not interfere with advancement of the catheter 608 through the manifold 604. Once suctioning has been completed, the catheter 608 is withdrawn into the collar 634. The plunger 624 is then pressed so as to move the shroud 620 over the distal end 634*a* of the collar 634 to cover the distal end 608*a* of the catheter 608. Typically, the catheter 608 will then be advanced toward the distal end 620*a* of the shroud 620. Lavage/cleaning solution will then be applied through the lavage port 640 while suction is applied.

If desired, a small gap can be formed between the shroud 620 and the collar 634 to ensure turbulent airflow into the distal end 608*a* of the catheter 608. Likewise, grooves or some other pattern may be formed in the shroud to encourage turbulent airflow. Additionally, a valve member may be included to allow for makeup air in a similar manner as discussed with several of the embodiments above.

Figure 9A:
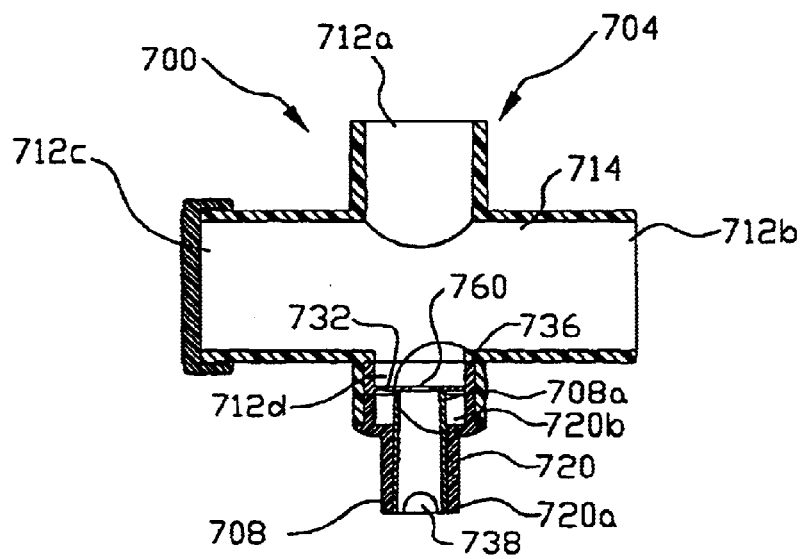
FIG. 9A shows a fragmented, cross-sectional view of an improved endotracheal catheter wherein the valve mechanism locks in a closed position.

Turning now to FIG. 9A, there is shown a fragmented, cross-sectional view of an alternate embodiment of an improved endotracheal catheter system, generally indicated at 700, incorporating aspects of the present invention. The endotracheal catheter system includes a manifold, generally indicated at 704, and a catheter 708. As with several of the previous embodiments, the manifold 704 includes a plurality of ports 712*a*–712*d*. The first port 712*a* is configured for attachment to the proximal end of an artificial airway, such as the hub of an endotracheal tube, tracheostomy tube, etc. A second port 712*b* is typically connected to a pair of ventilator tubes (not shown) by means of an adaptor (not shown), in accordance with common practice in the art. During normal usage, conditioned inspiratory air is forced through one of the ventilator tubes, through the second port 712*b* and the first port 712*a* and into the patient's lungs via the artificial airway. Exhaled air is carried through the first port 712*a* and then the second port 712*b* and out through the other ventilator tube. Thus, the manifold 704 forms part of a ventilation circuit 714 through which respiratory air is cycled.

Also forming part of the manifold 704 is a third port 712*c*. The third port 712*c* is typically covered by a cap 716 which may be removed to facilitate "blow-by" and thereby enable the patient to gradually resume spontaneous breathing. Those skilled in the art will appreciate that while the provision of a third port for blow-by is preferred, it is not necessary to the practice of the principles of the invention. Thus, a manifold similar to that shown in FIGS. 6A and 7A or some other manifold configuration could be used.

The manifold 704 also has a fourth port 712*d*. The fourth port 712*d* is disposed generally opposite the first port 712*a* and is configured to allow the catheter 708 to slide therethrough and into the first port to enable suctioning of the patient. At the completion of suctioning, the catheter 708 is pulled back into the fourth port 712*d* to facilitate cleaning and to prevent interference with the ventilation circuit 714.

Disposed between the wall forming the fourth port 712*d* and the catheter 708 is a coupling or adapter 720. On an outer extreme, the adapter 720 engages the wall defining the fourth port 712*d*. On an inner extreme, the adapter 720 engages the catheter 708. (If desired a collar -such as that shown in FIG. 3A at 224 could be used between the catheter 708 and the adapter 720).

The adapter 720 preferably has a cylindrical hollow which forms a first portion 720*a* disposed toward a proximal end thereof, and a second portion 720*b* disposed toward a distal end thereof. At the first portion 720*a*, the diameter of the cylindrical hollow is substantially the same as the outer diameter of the catheter 708 so that the first portion 720*a* of the adapter 720 closely surrounds the catheter.

The second portion 720*b* of the adapter's cylindrical hollow has a larger diameter than the first portion 720*a*. This larger diameter forms a collection area in which mucus and other secretions can collect as the catheter 708 is drawn proximally through the adapter 720.

As has been mentioned previously, in accordance with one of the principles of the present invention it has been found that selective obstruction of the airflow into the distal end 708*a* of the catheter 708 can significantly improve catheter cleaning. Additionally, it has been found that such a mechanism for improved cleaning also minimizes the withdrawal or air from the ventilation circuit 714.

As shown in FIG. 9A, a flap 732 is hingedly attached to an annular ring 736 disposed inside the fourth port 712*d* so as to enable the flap 732 to pivot with respect to the ring. Of course, the flap 732 could be attached directly to the wall of the manifold 704 defining the fourth port 712*d* or to the adapter 720. The hinged attachment allows the flap 732 to selectively move while maintaining alignment with the distal end 708*a* of the catheter 708, thereby creating a flap valve.

Disposed in the flap 732 is an aperture 760 which is positioned to provide a small amount of air into the interior of the distal end 708*a* of the catheter 708. As with previous embodiments, the aperture 760 provides a small amount of air into the catheter 708 to facilitate cleaning without drawing excessive air from the inhalation circuit of the patient.

With the flap 732 occluding airflow into the distal end 708*a* of the catheter 708, increased suction is applied to the lateral openings 738 which are formed in the catheter proximal from the distal end. The increased suction, in turn, creates improved cleaning of the catheter 708.

One significant difference between the flap 732 and those shown in previous embodiments is the manner in which it engages the ring 736. On one end, the flap 732 is pivotably attached to the ring 736 to enable movement as a flap valve as discussed above. At an opposing end, the flap 732 is configured to engage a flange 764 which extends inwardly from the ring 736. More specifically, the ends of the flap 732 and the flange 764 are configured to complement one another so as to nest in one another or otherwise form a locking engagement. Thus, as shown more clearly in FIG. 9B, the end 764*a* of the flange 764 is provided with a V-shaped groove and the complimentary end 732*a* of the flap 732 is V-shaped projection.

As the catheter 708 is withdrawn through the adapter 720 to the point where the distal end 708*a* of the catheter is disposed behind the ring 736, the suction of air through the tube will cause the flap 732 to be pulled into contact with the distal end of the catheter and thereby improve cleaning of the catheter as has been discussed with previous embodiments. Once the catheter 708 is sufficiently withdrawn through the adapter 720, the end 732a of the flap 732 will nest in the groove in the end 764a of the flange 764, thereby locking the flap in a closed position. With the flap 732 locked closed, the risk of mucus or other materials coming back into the ventilation circuit 714 is significantly reduced.

Thus, the engagement between the flap 732 and the flange 764 provides a locking mechanism which prevents flap 732 from being moved from the closed position (FIG. 9B) to the open position wherein the flap 732 does not interfere with distal movement of the catheter 708. With some of the prior embodiments, the only mechanism for maintaining the flap 732 in the closed position is via suction. In contrast, the present embodiment provides a positive retention of the flap 732 in the closed position.

When the next suctioning procedure is desired, the flap 732 can be opened by advancing the distal end 708a of the catheter 708 and forcing the end 732a of the flap out of engagement with the flange 764. The amount of force required is minimal above that normally exerted to advance the catheter for suctioning.

Figure 9B:
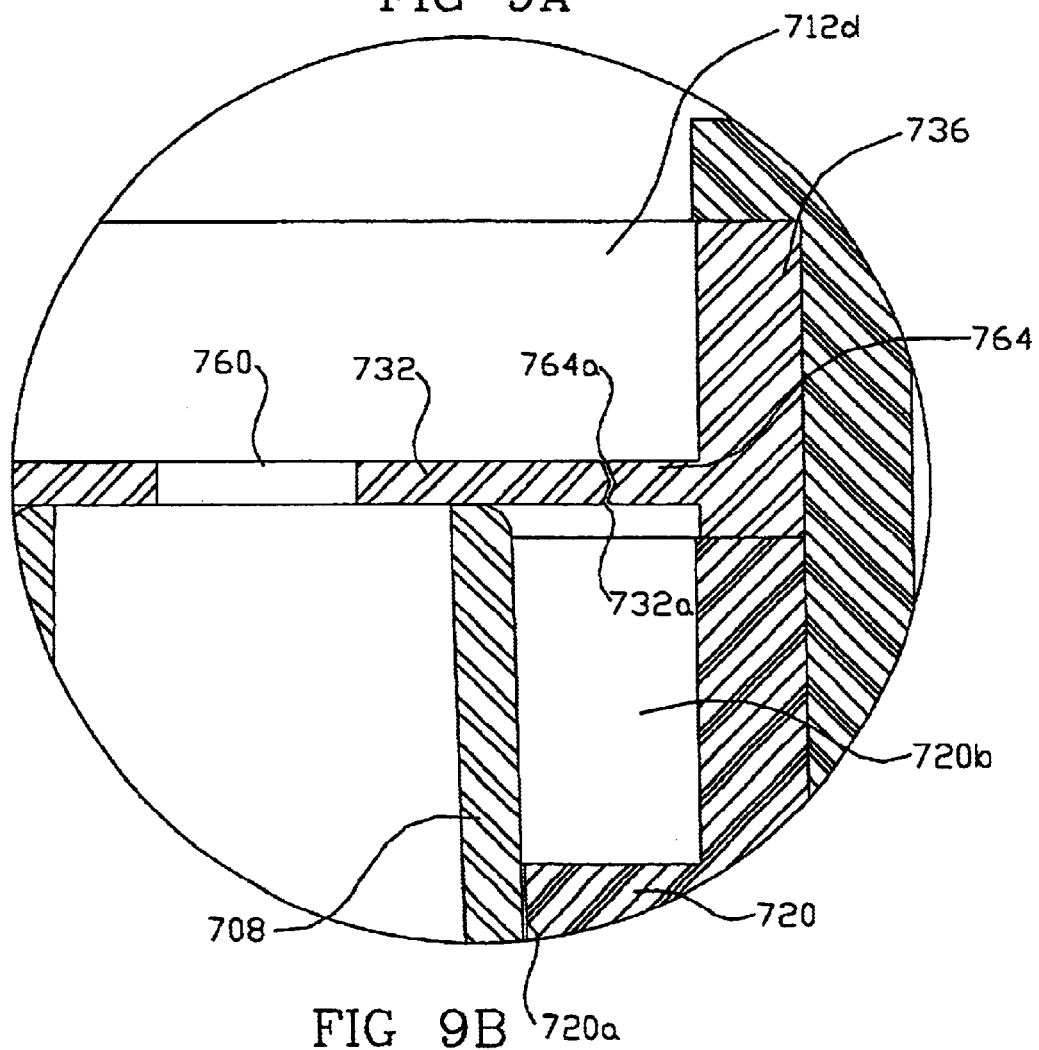
FIG. 9B shows a close-up view of the locking valve mechanism and associated structure of FIG. 9A.

While not shown in FIGS. 9A and 9B, a lavage port could be used with the adapter 720 to enhance cleaning of the catheter 708. The lavage port could be placed along either the first or second portions, 720a and 720b, depending on the tolerances thereof.

Figure 10A:
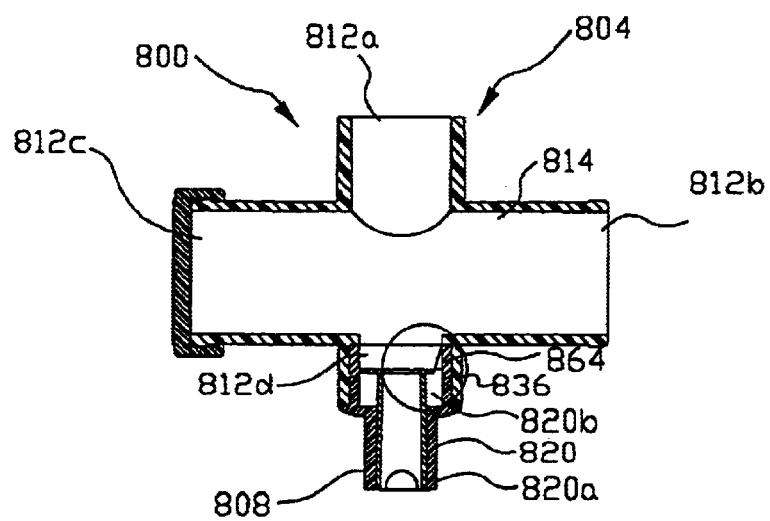
FIG. 10A shows a fragmented, cross-sectional view of an alternate embodiment of an improved endotracheal catheter with a locking valve mechanism.

Turning now to FIG. 10A, there is shown a fragmented, cross-sectional view of an alternate embodiment of an improved endotracheal catheter system, generally indicated at 800. As with the previous embodiment, the endotracheal catheter system includes a locking valve mechanism, generally indicated at 810.

The endotracheal catheter 800 includes a manifold, generally indicated at 804 and the catheter 808. The manifold includes first, second, third and fourth ports, 812a–812d which define a ventilation circuit 814 and otherwise function in the same manner as the first through fourth ports 712a–712d discussed above.

An adapter 820 is disposed in the fourth port 812d in a manner similar to that discussed with respect to the prior embodiment. The adapter 820 may include first and second portions 820a and 820b having different diameters to facilitate collection of mucus and other secretions, and to otherwise improve the workings of the device.

Also disposed in the fourth port 812d is a flap 832 which is configured to engage the distal end of the catheter 808. The flap 832 is pivotably attached to a ring 836 disposed in the fourth port 812d. (Of course, the flap 832 could be directly connected to the wall defining the fourth port 812d). As with several of the previously discussed embodiments, the flap 832 is drawn into contact with the distal end 808a of the catheter 808 as suction is applied through the catheter and the catheter is drawn proximally through the adapter 820. Preferably, an aperture 860 is formed in the flap 832 so that the flap provides resistance to airflow into the distal end 808a of the catheter 808 without completely terminating airflow. The reduced airflow improves cleaning, while complete lack of airflow can inhibit the same. The size of the aperture 860 is preferably about 0.03 inches in diameter.

Also disposed on the ring 836 is an inwardly extending projection 864 which forms a catch. Preferably, the projection 864 is disposed on the ring 836 opposite the location at which the flap 832 is attached to the ring. (As with the flap 832, the projection could also be directly mounted on in the fourth port 812d).

As the flap 832 is drawn proximally by suction through the catheter 808, the flap passes over the projection 864 which extends inwardly slightly further than the end 832a of the flap. Thus, once the flap 832 has moved proximally beyond the extreme inward point of the projection 864, distal movement of the flap is restricted by the projection. Thus, the flap 832 becomes frictionally engaged behind the projection 864 until is forced distally past the projection by advancement of the catheter 808. (While discussed above as requiring suction, those skilled in the art will appreciate that the flap 832 (etc.) could be configured to bias the flap into the proximal or closed position.)

Figure 10B:
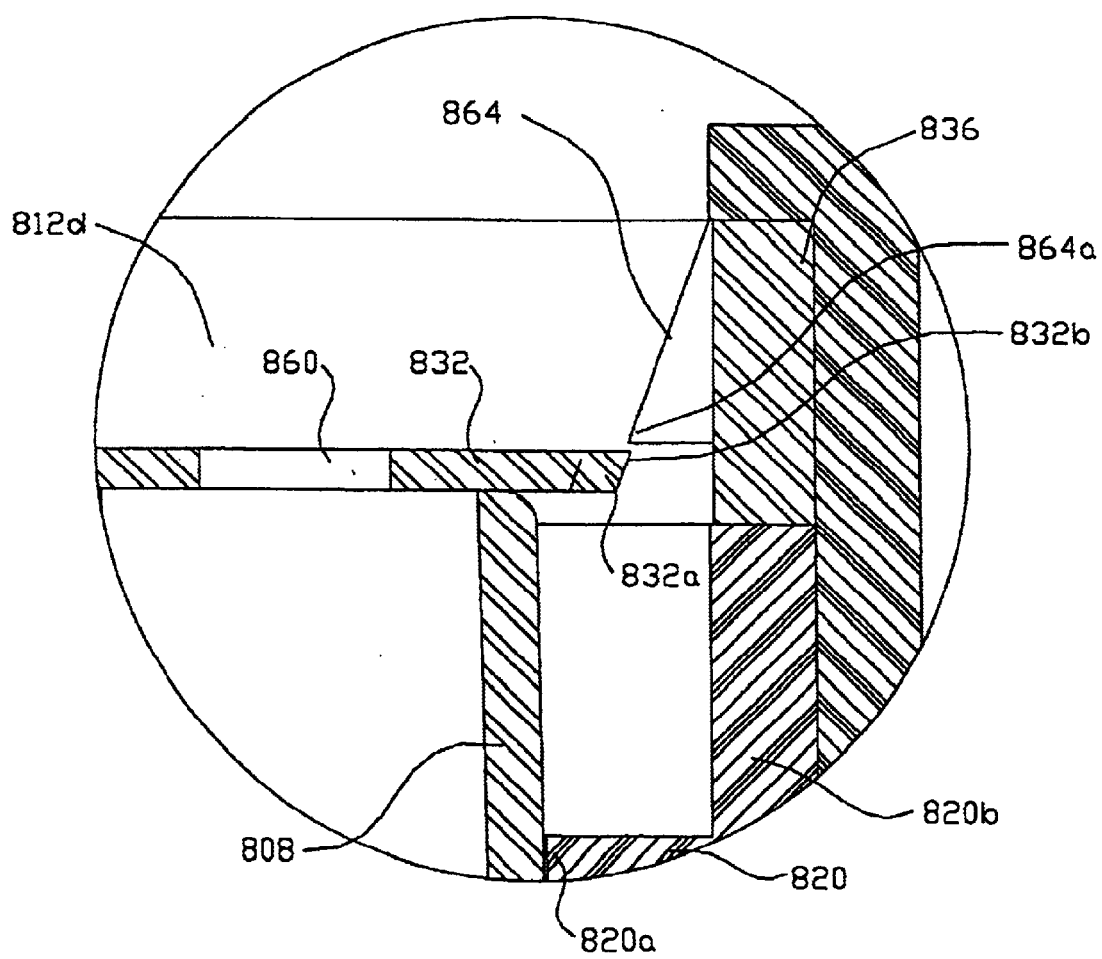
FIG. 10B shows a close-up view of the locking valve mechanism and associated structure of FIG. 10A.

Referring specifically to FIG. 10B, there is shown a close-up view of the locking valve mechanism and locking structure discussed above. As shown, the end 832a of the flap 832 is tapered to a point 832b which is formed on the distal side of the flap. The projection 864 tapers toward a point disposed at the proximal end 864a thereof. Such a configuration enables the end 832a of the flap 832 to slide proximally over the projection 864, while requiring additional effort to move the flap distally past the projection.

FIG. 11A shows a cross-sectional view of yet another embodiment of an improved endotracheal catheter, generally indicated at 900. The catheter 900 includes a manifold 904 and a catheter 908. The manifold 904 includes first, second, third and fourth ports, 912a–912d, the first and fourth of which are aligned to allow advancement of the catheter 908 through the manifold.

An adapter 920 is disposed in the fourth port 912d and functions as a guide for the catheter 908 as it is advanced and retracted. The adapter 920 preferably includes a first portion 920a having a inner diameter approximately the same size as the outside diameter of the catheter 908, and a second portion 920b having a diameter which is larger than that of the first portion.

Also disposed in the fourth port 912d is a pair of rings 936a and 936b. A flap 932 is attached to the ring 936b and extends inwardly so as to be disposed perpendicular to the travel path of the catheter 908 as it is advanced through the manifold 904. The flap 932 preferably has a small hole 960 to allow a small amount of air through the flap 932.

Referring more specifically to FIG. 11B, the flap 932 is pivotably attached to the ring 936b so that as the distal end 908a of the catheter 908 is withdrawn through the fourth port 912d, suction from the catheter draws the flap 932 into contact with the distal end 908a. In such a manner, the flap 932 functions as a flap valve to substantially occlude the distal end of the catheter 908.

Also shown more clearly in FIG. 11B is a catch 964 which is attached by an arm 968 to the ring 936a. The catch 964 is configured to engage the flap 932 to lock the flap in a desired location. As the catheter 908 is withdrawn through the fourth port 912b, the flap 932 is drawn to the distal end 908a and drawn proximally by the suction through the catheter. (Biasing could also be used). The end 932a of the flap 932 opposite the attachment point 940 between the flap and the ring 936b engages the catch 964 and causes the catch to be deflected out of the way (to the right in FIG. 11B). Once the end 932a of the flap 932 has passed by the catch 964, the catch moves back into its normal position. In such a position, the catch 964 engages the end 932a of the flap 932 and locks the flap in a proximal, closed position. To release the flap 932, the catheter 908 is advanced with sufficient force to cause the catch 964 to deflect out of the way. The flap 932 may then pivot distally and the catheter 908 advanced.

Turning now to FIG. 11C, there is shown an end view of the flap 932, the rings (shown jointly as 936) and associated structure. The flap 932 is attached to the ring 936 by two arms 948, each forming an attachment point 940. The opposite end 932a of the flap 932 engages the catch 964 which is attached to the ring 936 by an arm 968. The catch 964 effectively locks the flap 932 in a proximal position until the user forcibly advances the catheter in a distal direction, causing the catch to release the flap.

Those skilled in the art will appreciate that numerous modifications could be used to accomplish the principles of the present invention. As an example, a single arm 948 could be used with the flap 932, and multiple catches 964 could be used. Likewise, a single ring could be used rather than the first and second rings 936a and 936b to support the flap 932 and the catch 968. Furthermore, as is shown in FIG. 11D, modifications can be made the flap 932' to provide other benefits.

Figure 11D:
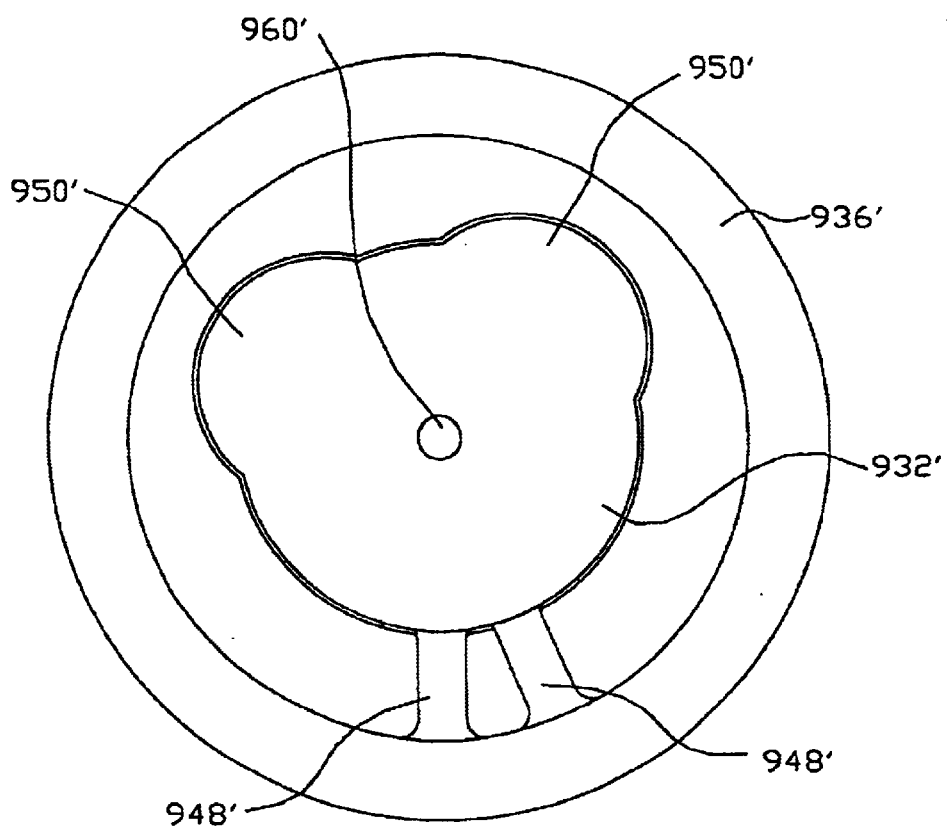
FIG. 11D shows a close-up end view of an alternate embodiment of the flap shown in FIG. 11C.

As shown in FIG. 11D, the flap 932' is attached to the ring 936' by a pair of arms 948'. As mentioned above, the arms 948' could be configured to bias the flap 932' into the closed position.

The flap 932' is generally circular, but has two rounded projections 950' which extend outwardly and are spaced approximately 90 degrees apart. The projections serve two important purposes. First, even if the generally circular portion of the flap 932' were slightly smaller than the distal opening of the endotracheal tube (not shown), the projections 950' would prevent the flap from entering the endotracheal tube. Second, the projections 950' would cause the flap to align for air flow to continue to the patient without laying flat to cover any passage which might interfere with airflow to or from the patient.

Also shown in FIG. 11D is the aperture 960' which is formed in the generally circular portion of the flap 932'. As shown the aperture 960' is between 0.03 and 0.04 inches in diameter. While shown as being circular or disk-shaped, those skilled in the art will appreciate, in light of the present disclosure, that other shaped apertures could also be used.

Figure 12A:
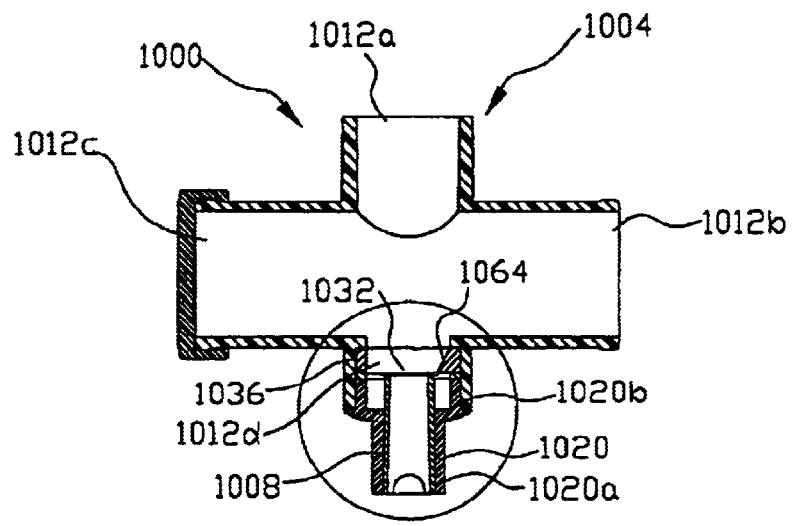
FIG. 12A shows a fragmented, cross-sectional view of yet another embodiment of an improved endotracheal catheter which has a locking mechanism disposed thereon.

Turning now to FIG. 12A, there is shown a side cross-sectional view of an improved endotracheal catheter, generally indicated at 1000. The improved endotracheal catheter 1000 includes a manifold, generally indicated at 1004, and a catheter 1008. The manifold 1004 includes first, second, third and fourth ports 1012a–1012d as set forth above.

An adapter 1020 is disposed in the fourth port 1012d and facilitates advancement and withdrawal of the catheter through the manifold 1004. While shown as having a first portion 1020a with a smaller diameter and a second portion 1020b with a larger diameter, the adapter 1020 could be made with a uniform interior diameter. In the alternative, the wall defining the fourth port 1012d could be configured to eliminate the need for an adapter.

Also disposed in the fourth port 1012d is a flap 1032 which is connected to a ring 1036. The flap 1032 extends inwardly from the ring 1036 and is configured to be disposed perpendicular to the long axis of the catheter 1008.

Figure 12B:
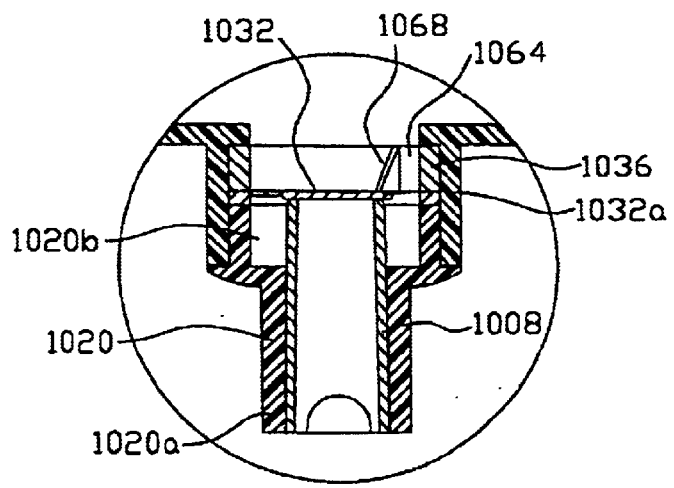
FIG. 12B shows a close-up view of the locking valve mechanism and associated structure of FIG. 12A.

Like the previous embodiment, the end 1032a of the flap 1032 engages a catch mechanism 1064 which extends inwardly. As shown more clearly in FIG. 12B, the catch mechanism 1064 is formed by at least one projection 1068 which extends proximally and inwardly from the ring 1036. As the flap 1032 is drawn proximally by the catheter 1008, the end 1032a of the flap is drawn over the projection 1068 which temporarily deflects. Once the flap 1032 has moved a sufficient distance proximally, the projection 1068 returns to its normal position and thereby locks the flap in the proximal position.

Figure 12C:
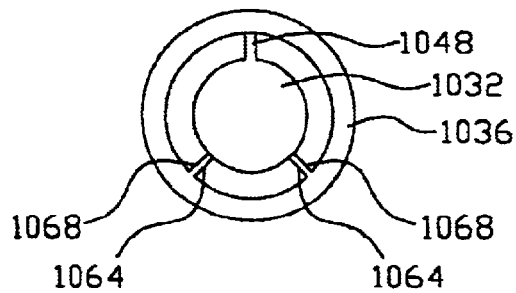
FIG. 12C shows a close-up end view of the locking valve mechanism of FIGS. 12A and 12B.

FIG. 12C shows an end view of the ring 1036 and the flap 1032. The flap 1032 is attached to the ring 1036 by a single arm 1048. A pair of catch mechanisms 1064 in the form of projections 1068 are spaced apart at 120 degree intervals. Having the catch mechanisms 1064 spaced helps to stabilize the flap 1032 when in the locked position.

Figure 13A:
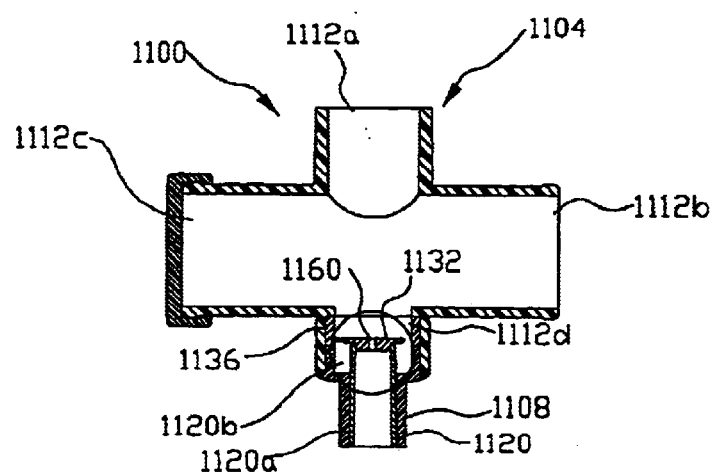
FIG. 13A shows a fragmented, cross-sectional view of an alternate embodiment of an improved endotracheal catheter with a locking valve mechanism.

Turning now to FIG. 13A there is shown a fragmented, cross-sectional view of an alternate embodiment of an improved endotracheal catheter, generally indicated at 1100. The endotracheal catheter 1100 includes a manifold, generally indicated at 1104 and a catheter 1108. The manifold 1104 includes first, second, third and fourth ports 1112a–1112d which enable ventilation and other procedures through the manifold.

Disposed in the fourth port 1112d is an adapter 1120. The adapter 1120 is configured to receive the catheter 1108 as it is advanced and retracted through the manifold 1104. The adapter 1120 includes a first portion 1120a wherein the interior diameter of the adapter is only slightly larger than the exterior diameter of the catheter, and a second portion 1120b wherein an open area is left around the catheter 1108.

Also disposed in the fourth port 1112d of the manifold 1104 is a flap 1132 pivotably attached to a ring 1136. (As with several of the previously discussed embodiments, the ring could be omitted and the flap directly attached to the manifold). The flap 1132 pivots to selectively occlude the distal end 1108a of the catheter 1108. To prevent complete termination of airflow into the distal end 1108a of the catheter 1108, however, an aperture 1160 is formed in the flap 1132.

Unlike the embodiments discussed above with respect to FIGS. 9A through 12B, the flap 1132 does not engage a flange or projection on the ring 1136. Rather, the flap 1132 is provided with an projection 1132a disposed on the flap's proximal side. The projection 1132a has an outer diameter which is substantially the same as the inner diameter of the distal end 1108a of the catheter 1108.

As suction is applied through the catheter 1108 and it is withdrawn through the fourth port 1112d, the projection 1132a is drawn into the distal end 1108a of the catheter 1108 where it forms a friction fit between the flap 1132 and the catheter.

Figure 13B:
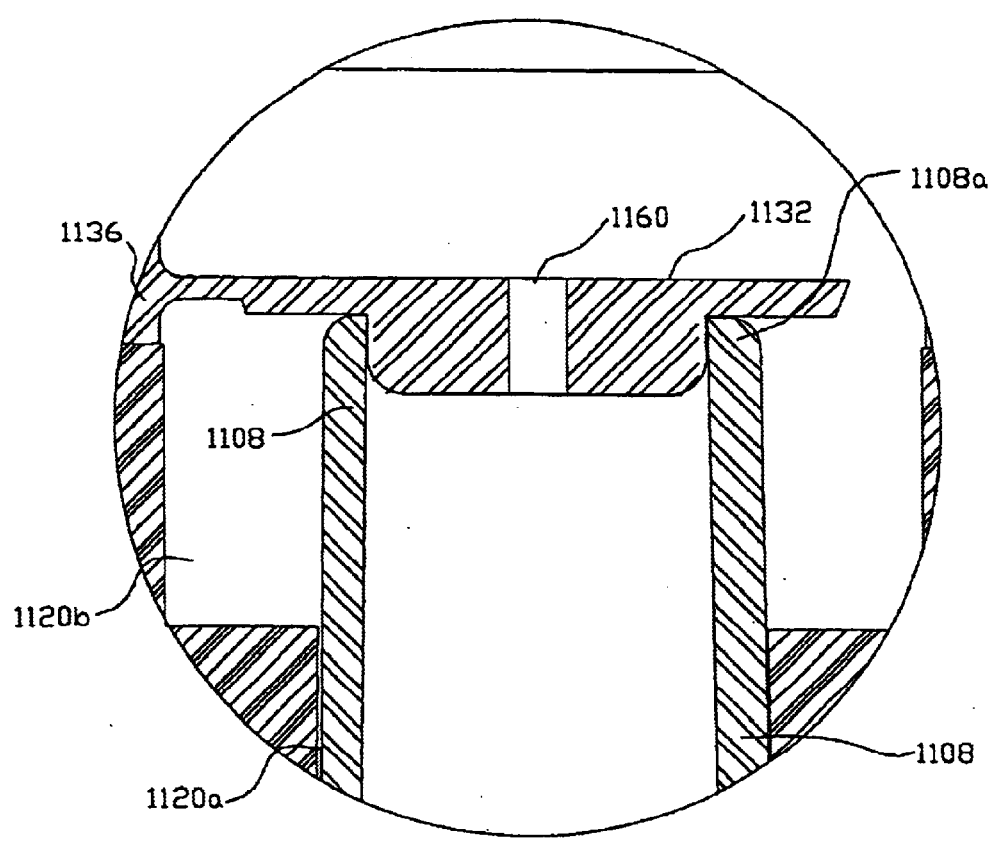
FIG. 13B shows a close-up view of the locking valve mechanism and associated structure of FIG. 13A.

Turning now to FIG. 13B, there is shown a shown a close-up view of the flap/catheter engagement of FIG. 13A. The proximally extending projection 1132a of the flap 1132 nests in the open distal end 1108a of the catheter 1108 to restrict airflow through the open distal end. Air flow continues, of course, through lateral openings (such as those shown in FIGS. 3A–3D) in the catheter 1108. The projection 1132a of the flap 1132 can be removed from the catheter 1108 by either advancing the catheter through the fourth port 1112d and having the flap 1132 pull the projection 1132a from the catheter, or by withdrawing the catheter proximally until the projection is pulled from catheter.

Figure 13C:
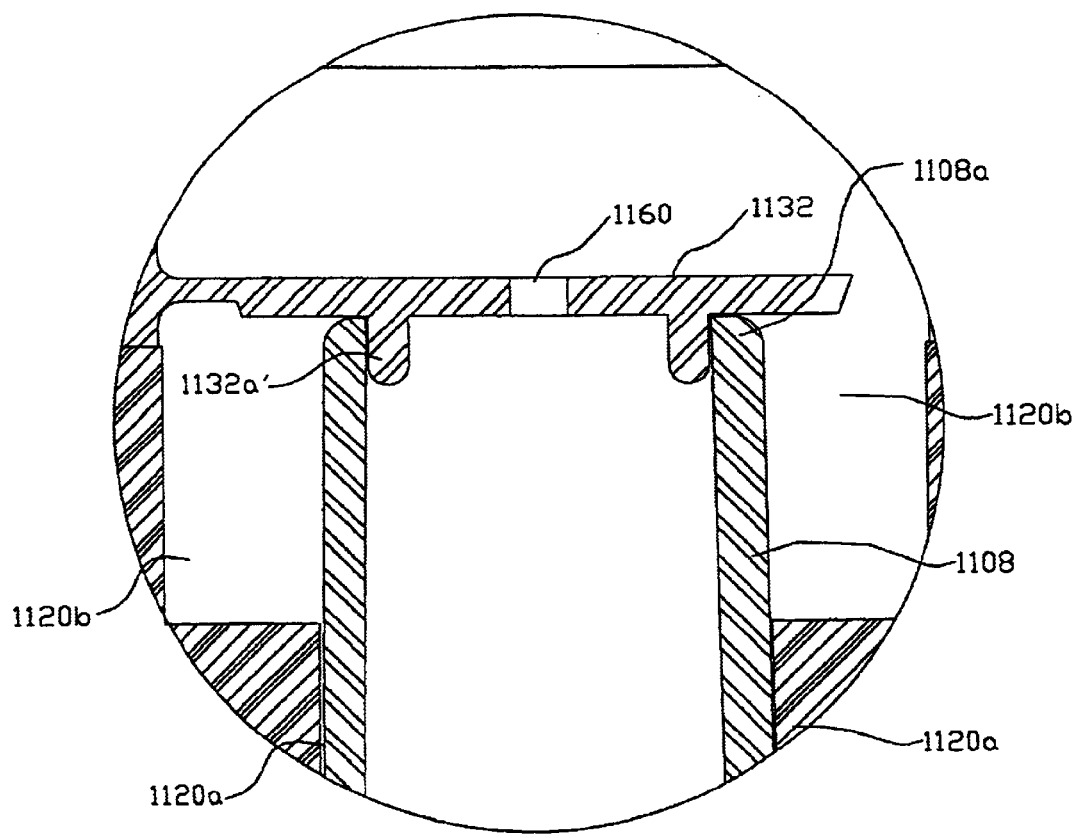
FIG. 13C shows a close-up view of the locking valve mechanism and associated structure of FIG. 13A in which the flap is modified from that shown in FIG. 13B.

Turning now to FIG. 13C, there is shown a close-up view of the flap/catheter engagement of FIG. 13A with a modification to the flap 1132. While the view of FIG. 13B shows a projection which is solid except for the aperture 1160, those skilled in the art will appreciate that any configuration which enables a friction fit between the projection and the distal end 1108a of the catheter 1108 will work. Thus, in FIG. 13C, the projection 1132a' is formed by an annular flange which extends proximally from the flap 1132. Other configurations may also be used.

Figure 14A:
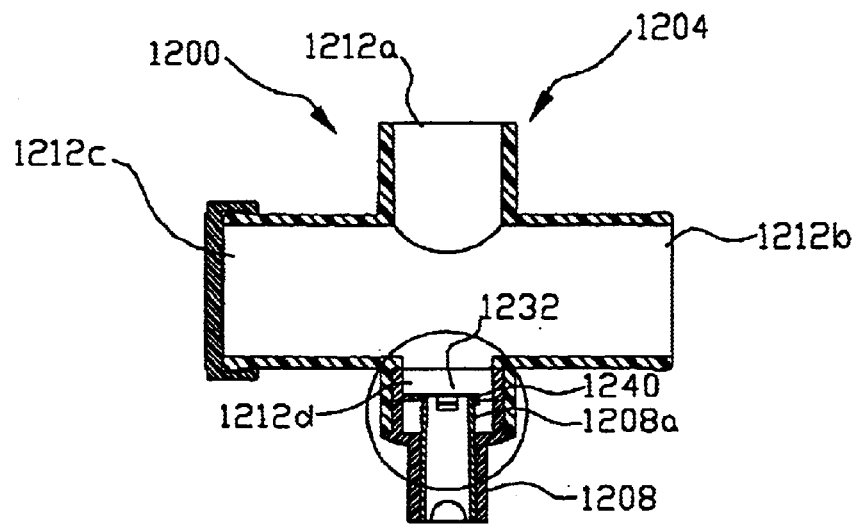
FIG. 14A shows a fragmented, cross-sectional view of an alternate embodiment of an improved endotracheal catheter with a locking valve mechanism.

Turning now to FIG. 14A, there is shown a fragmented, partially cut away, cross-sectional view of yet another alternate embodiment of an improved endotracheal catheter, generally indicated at 1200. The endotracheal catheter 1200 includes a manifold, generally indicated at 1204 and a catheter 1208. The manifold 1204 includes first, second, third and fourth ports 1212a–1212d which function in the same manner discussed above with respect to other embodiments.

An adapter 1220 is disposed in the fourth port 1212d so that the catheter 1208 reciprocates through the adapter as it is advanced into and withdrawn from the manifold 1204. As with several embodiments discussed above, the adapter 1220 may have a first portion 1220a defining a first diameter slightly larger than the catheter 1208 and a second portion 1220b defining a larger area around the catheter.

Also disposed in the fourth port 1212d is a flap 1232 configured to engage the distal end 1208a of the catheter. The flap 1232 is typically pivotably attached by an arm 1248 to a ring 1236 which is also disposed in the fourth port 1212d. However, the flap 1232 could be directly attached to the wall defining the fourth port, or anchored in some other way.

Figure 14B:
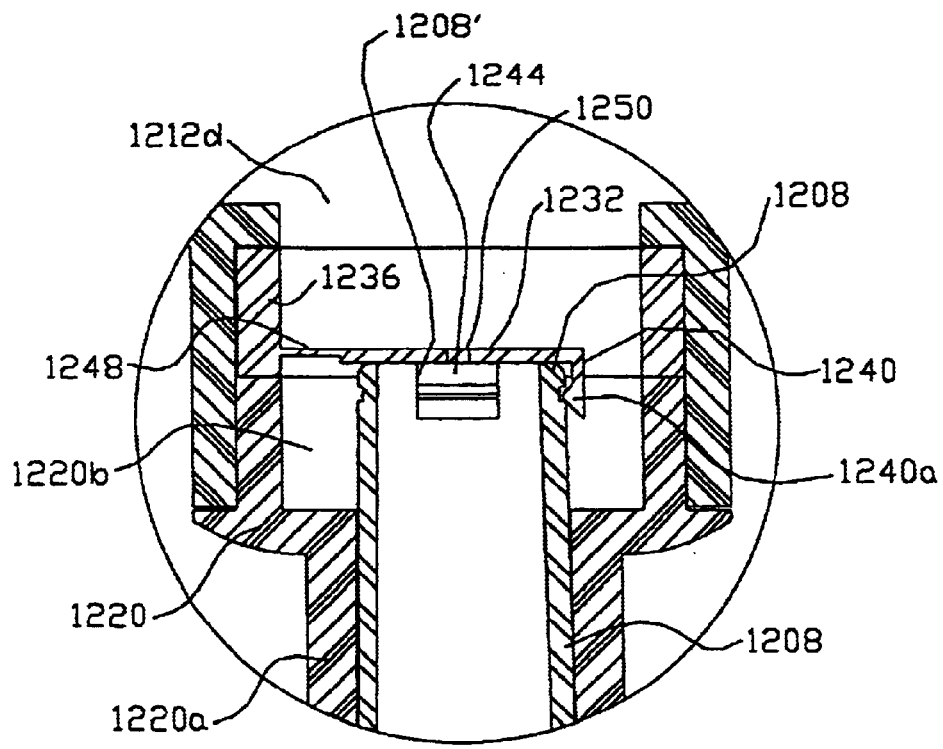
FIG. 14B shows a close-up view of the locking valve mechanism and associated structure of FIG. 14A.

Referring to FIG. 14B, there is shown a close-up view of the structures within the fourth port 1212d. The pivoting function of the flap 1232 is similar to many of the embodiments discussed above, in that the flap is drawn into contact with the distal end 1208a of the catheter 1208 as the catheter is withdrawn through the fourth port 1212d. Unlike the prior embodiments, however, the flap 1232 includes a pair of catches 1240 which extend proximally from the flap.

As shown in FIG. 14B, one of the catches 1240 is disposed at the right side of the catheter 1208, while the other is made visible by the cutaway portion 1208' of the catheter. While the catches 1240 are disposed so that one catch is positioned 90 degrees from the arm and the other catch 180 degrees from the arm, it is presently understood that the preferred positioning of the catches is for them to be disposed 180 degrees from each other, which each catch being 90 degrees from the arm 1248.

The catch 1240 engages the distal end of the catheter 1208, to form a locking mechanism wherein the flap 1232 is held to the distal end 1208a of the catheter 1208 until being forcibly removed therefrom. Typically, this is accomplished by using catches 1240 which are biased slightly inwardly so that a barb 1240a on the catch engages an annular groove 1208b positioned in the outer diameter of the distal end of the catheter 1208. As suction is applied and the flap 1232 is drawn toward the distal end of the catheter 1208 and each catch 1240 slides along the catheter until it engages the groove 1208b. Once engaged, the flap 1232 remains locked to the distal end of the catheter 1208 until the catheter is moved sufficiently in either direction to pull the catch 1240 from the groove 1208b.

As with the prior embodiments, the flap 1232 preferably has a small hole 1248 disposed therein. The hole 1250 allows a small amount of airflow into the catheter 1208 through the flap.

Figure 14C:
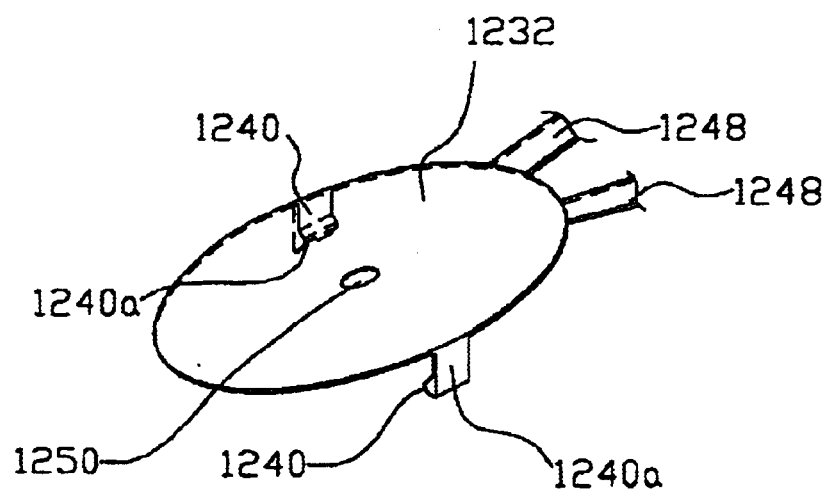
FIG. 14C shows a perspective view of the flap shown in FIGS. 14A and 14B.
Figure 14D:
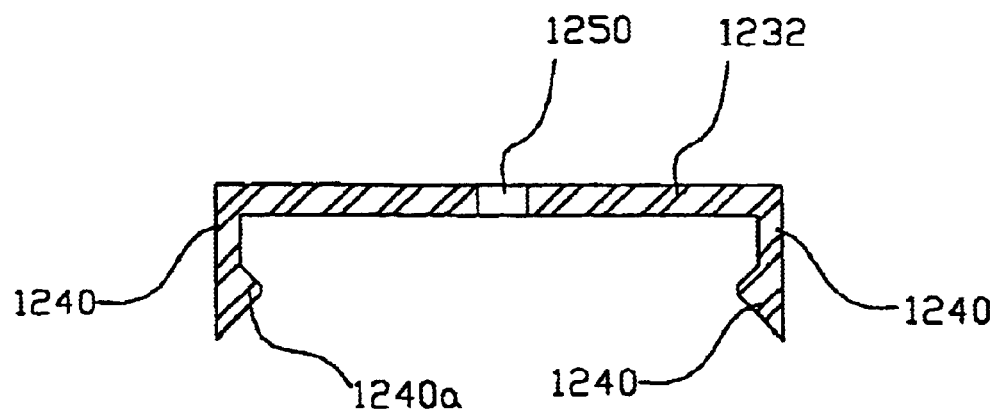
FIG. 14D shows a side view of the flap shown in FIGS. 14A through 14C.

Turning now to FIGS. 14C and 14D, there is shown a perspective view, and a side view of a presently preferred embodiment of the flap 1232 shown in FIGS. 14A and 14B. The flap 1232 is attached to the ring (not shown) by the arm 1248, and has a pair of catches 1240 which extend proximally (downwardly as shown in the drawing) to engage the catheter (not shown) and thereby lock the flap to the catheter. Preferably, the catches have barb 1240a configured to nest in a groove or detent in the catheter (not shown). As mentioned above, the catches 1240 are positioned 180 degrees from each other, with each being 90 degrees from the arm 1248.

Figure 15A:
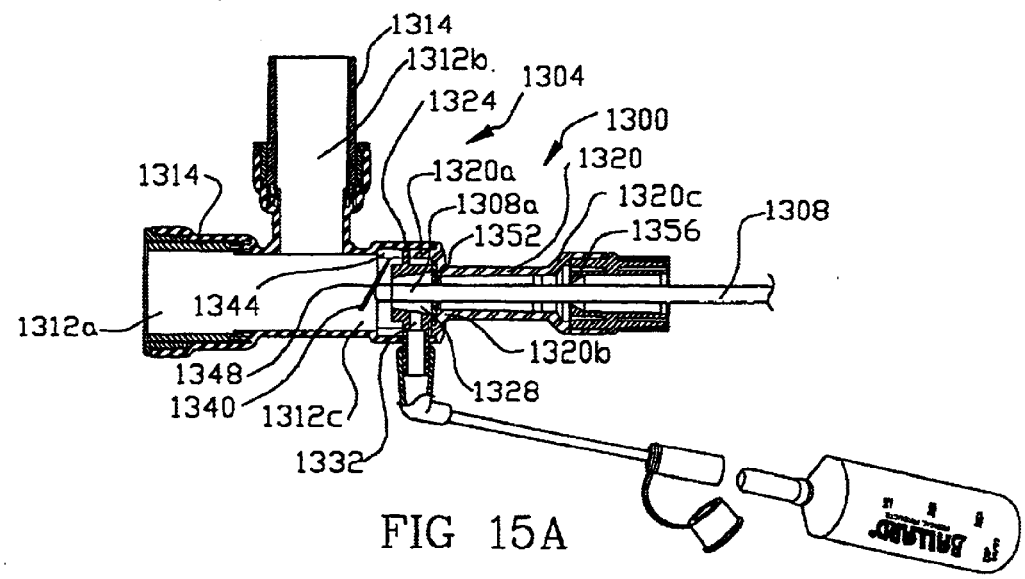
FIG. 15A shows a fragmented, cross-sectional view of an alternate embodiment of an improved endotracheal catheter in which a pair of wiper seals are used to enhance cleaning of the distal end of the catheter tube.

FIG. 15A shows a cross-sectional view of yet another embodiment of an endotracheal catheter system 1300 which incorporates aspects of the present invention. The endotracheal catheter system 1300 includes a manifold, generally indicated at 1304 which forms a fitting for connecting the endotracheal catheter 1300 to the artificial airway (i.e. endotracheal tube) of a patient. The endotracheal catheter system 1300 also includes an elongate catheter 1308.

The manifold 1304 includes a first port 1312a, a second port 1312b and a third port 1312c. The first port 1312a is configured to engage an artificial airway, such as an endotracheal tube. The second port 1312b provides inspiratory and expiratory airflow to and from the patient. Typically, a Y-shaped adapter is attached to the second port 1312b. However, many configurations are used in the clinical setting and those skilled in the art will appreciate the different combinations which are available.

The third port 1312c is disposed opposite the first port 1312a and aligned so that the catheter 1308 can pass through the third port, through the manifold 1304 and through the first port into the artificial airway. As shown in FIG. 15A, the first and second ports 1312a and 1312b may also have swivel structures 1314 to enable the manifold 1304 to swivel with respect to adjoining structures and thereby improve patient comfort.

Connected to the third port 1312c is a coupling or adapter 1320. On the outer surface of the distal end 1320a, the adapter 1320 engages the wall defining the third port 1312c. The inner surface of the adapter 1320 forms a chamber about the distal end 1308a of the catheter 1308. This chamber assists in cleaning the distal end of the catheter in a manner which will be discussed more fully below.

Disposed adjacent to the distal end 1320a of the adapter 1320 is a collar 1324 which has a frustoconical bore 1328 extending therethrough. (Those skilled in the art will appreciate that the collar 1324 could be formed integrally with the adapter 1320 if desired).

When lavage solution is injected through a lavage port 1330 and a side opening 1332 into the frustoconical bore 1328, the collar 1324 helps to channel the lavage solution along the catheter 1308, through the first port 1312a and into the artificial airway.

The distal end of frustoconical bore forms an orifice in the distal end of the collar 1324. A flap 1340, supported by a support ring 1344 disposed in the third port 1312c selectively engages the orifice to substantially occlude the orifice when the two are engaged. As with prior embodiments, the flap 1340 preferably has one or more holes 1348 formed therein to allow a small amount of air through the flap. Also, like prior embodiments, the flap 1340 may be biased in the occluding position, or may be drawn into the occluding position by suction through the catheter 1308.

Disposed at the opposing, proximal end of the collar 1324 is a first wiper seal 1352. Preferably, the wiper seal 1352 is supported by a narrowed portion 1320b of the adapter 1320. Those skilled in the art, however, will appreciate that other mechanism for holding the wiper seal 1352 could be used. As the catheter 1308 is withdrawn past the first wiper seal 1352, the wiper seal removes major secretions. While discussed herein as a wiper seal, some other structure having close tolerances (i.e. one which would remove most secretions) could also be used.

From the wiper seal 1352, the adapter 1320 extends proximally and forms a cleaning chamber. Disposed adjacent a proximal end 1320c of the adapter 1320 is a second wiper seal 1356. As with the first wiper seal 1352, the object of the second wiper seal 1356 is to remove secretions from the exterior of the catheter 1308 as it is withdrawn from the artificial airway of the patient. However, the second wiper seal 1356 will typically have a smaller diameter opening so that the second wiper seal more closely engages the exterior of the catheter 1308 than the first wiper seal.

Conventionally, a single wiper seal has been used. The wiper seal was placed in the location of the second wiper seal 1356 to wipe secretions from the catheter as it was withdrawn. The distal most 0.5–1 inch of the catheter, however, was never physically wiped. Instead, the operator attempted to clean this portion with solution injected through a lavage port.

Figure 15B:
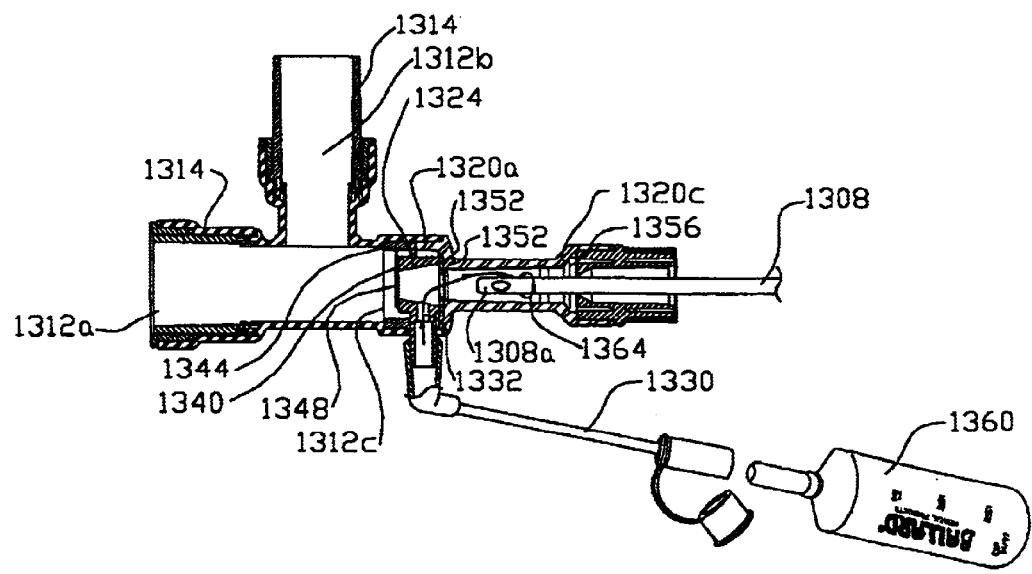
FIG. 15B shows a cross-sectional view similar to that of FIG. 15A, but with the catheter tube pulled back into a proximal position.

Turning now to FIG. 15B, there is shown a side cross-sectional view of the endotracheal catheter 1300 in which the catheter 1308 has been withdrawn through the manifold 1304 into a cleaning position. As the catheter 1308 is withdrawn, the flap 1340 closes (either due to a bias or the suction through the catheter) to occlude the opening in the collar 1324.

As the catheter 1308 is withdrawn proximally out of the collar 1324 and past the wiper seal 1352, the distal end 1308a of the catheter is wiped by the wiper seal 1352 so that most secretions thereon are removed. The secretions which are removed by the wiper seal 1352 are then carried through the catheter 1308.

Once the distal end 1308a of the catheter 1308 has advanced beyond the first wiper seal 1352, a bottle 1360 is attached to the lavage port 1330 and a cleaning liquid (typically water) is supplied through the side opening 1332 in the collar 1324. The cleaning liquid flows around the distal end 1308a of the catheter 1308, indicated by arrow 1364, and cleans those secretions which were not removed by the first wiper seal 1352 from the distal end of the catheter.

At the same time, the holes 1348 in the flap 1340 allow a small amount of air into the catheter, thereby facilitating removal of the secretions. If desired, a make-up air valve could be disposed on the side of the adapter 1320 to allow the inflow of additional air.

By use of these various configurations, the cleaning of the distal end of a catheter can be enhanced while minimizing or eliminating the air drawn from the ventilation circuit of the patient. Those skilled in the art will appreciate modifications which can be made without departing scope and spirit of the present invention. The appended claims are intended to cover such modifications.

What is claimed is:

1. An endotracheal suction catheter apparatus comprising:
   a catheter configured for removing fluids from a respiratory tract of a patient by applying negative pressure to a lumen of the catheter;
   a manifold defining a ventilation circuit disposed in communication with the catheter so as to allow the catheter to be advanced through the ventilation circuit of the manifold and into the respiratory tract of the patient, the manifold having a port with a longitudinal axis;
   a valve disposed in the manifold, the valve comprising a single flap hingedly attached to an annular ring, the single flap pivotable with respect to the annular ring and the valve configured to selectively limit the withdrawal of air from the ventilation circuit, the single flap being actuated by suction through the catheter, the single flap being movable between a first, open distal position and a second, proximal position in which the single flap is positioned substantially perpendicular to the longitudinal axis of the port of the manifold; and
   a biasing hinge biasing the single flap of the valve to the first distal position, the biasing hinge attached to the annular ring and the single flap.

2. The endotracheal suction catheter apparatus of claim 1, wherein the flap is configured for engaging the distal end of the catheter.

3. The endotracheal suction catheter apparatus of claim 2, wherein the valve further comprises a catch for holding the single flap in the second, proximal position.

4. The endotracheal suction catheter apparatus of claim 3, wherein the catch is disposed to engage the single flap as the flap is drawn into the second, proximal position and to retain the flap in the second, proximal position.

5. The endotracheal suction catheter apparatus of claim 3, wherein the catch is disposed on the single flap.

6. The endotracheal suction catheter apparatus of claim 1, wherein the single flap is pivotably connected to the manifold.

7. The endotracheal suction catheter apparatus of claim 1, wherein the single flap is generally disk-shaped and has at least one projection extending outwardly therefrom to increase the diameter of the disk.

8. The endotracheal suction catheter apparatus of claim 1, wherein the valve has an open position and a closed position and wherein the valve comprises means for frictionally maintaining the valve in the closed position.

9. The endotracheal suction catheter apparatus of claim 1, wherein said single flap having a channel formed on the proximal side of said flap in order to create increased turbulence about the distal end of the catheter.

10. The endotracheal suction catheter apparatus of claim 1, further comprising a first seal and a second seal disposed along the catheter when the catheter is advanced into the manifold.

11. The endotracheal suction catheter apparatus of claim 10, wherein the first seal is disposed distally from the second seal, and wherein a lavage port is disposed distally from the first seal.

12. An endotracheal catheter system comprising:
   an elongated catheter having a tubular portion with a distal end;
   a manifold defining a portion of a ventilator circuit disposed in communication with the catheter so as to allow the catheter to be advanced through the ventilator circuit of the manifold and into a respiratory tract of a patient, the manifold having an introduction port for allowing the catheter to be introduced into the manifold, the introduction port having a longitudinal axis;
   a self-closing valve member comprising a single flap which is moveable between open and closed positions and which is disposed adjacent the catheter to selectively isolate the catheter from the ventilator circuit in the manifold, the self-closing valve member being capable of being opened by insertion of said tubular portion of said catheter through the ventilator circuit of the manifold, wherein when the single flap is in the closed position the single flap is substantially perpendicular to the longitudinal axis of the introduction port of the manifold; and a biasing hinge biasing the single flap of the self-closing valve member to the closed position, the biasing hinge attached to the single flap.

13. The endotracheal catheter system of claim 12, wherein the self-closing valve member is disposed in the manifold.

14. The endotracheal catheter system of claim 12, wherein the self-closing valve member is moveable between an open position wherein the self-closing valve member permits advancement of the catheter through the manifold, and a closed position, wherein the valve member isolates the catheter from the ventilator circuit.

15. The endotracheal catheter system of claim 14, wherein the self-closing valve member closes responsive to suction applied through the catheter when the catheter is not advanced through the manifold.

16. The endotracheal catheter system of claim 14, wherein the self-closing valve member is biased in a closed position.

17. The endotracheal catheter system of claim 16, wherein the single flap is biased toward the closed position.

18. The endotracheal catheter system of claim 12, further comprising:
    a coupling having a distal end, said coupling connected to the manifold, the elongated catheter moving through the coupling when the elongated catheter is advanced through the ventilator circuit of the manifold and into a respiratory tract of a patient; and
    a collar disposed adjacent to the distal end of the coupling, the coupling having a frustoconical bore extending threrethrough, the distal end of the frustoconical bore forming an orifice in the distal end of the collar, the single flap of the self-closing valve member engaging the orifice when the elongated catheter is withdrawn from the ventilator circuit of the manifold.

19. The endotracheal catheter system of claim 18, further comprising a wiper seal disposed at the proximal end of the collar.

20. An endotracheal catheter system comprising:
    a catheter having a tubular portion with a distal end configured for suctioning secretions from a patient;
    a ventilator manifold disposed in communication with the catheter such that the catheter may be advanced through the manifold into the respiratory system of the patient and withdrawn from a respiratory system of the patient through the manifold, the manifold having a port with a longitudinal axis;
    a valve comprising a single pivotable flap disposed within the manifold for at least partially occluding the distal end of the catheter, the valve being configured to frictionally engage the distal end and thereby occlude the distal end, said valve capable of being opened by insertion of said tubular portion of said catheter into said manifold, the single flap being movable between a first, distal position and a second, proximal position in which the single flap is positioned substantially perpendicular to the longitudinal axis of the port of the manifold; and
    a biasing hinge biasing the single flap of the valve to the first distal position, the biasing hinge attached to the manifold and the single flap.

21. The endotracheal catheter system of claim 20, wherein the valve frictionally engages the distal end of the catheter responsive to negative pressure applied through the catheter.

22. The endotracheal catheter system of claim 21, wherein the single flap is configured to frictionally engage the distal end of the catheter.

23. An endotracheal suction catheter apparatus comprising:
    a catheter having a tubular portion with a distal end;
    a manifold disposed in communication with the catheter so as to allow the catheter to be advanced through the manifold into a respiratory tract of a patient;
    a valve having a single flap pivotable between open and closed positions which is configured for engaging the distal end of the catheter to thereby occlude suctioning through the distal end of the catheter, said valve capable of being opened by insertion of said tubular portion of said catheter into said manifold; and
    a biasing hinge biasing the single flap of the valve to the open position, the biasing hinge attached to the single flap.

24. The endotracheal suction catheter apparatus of claim 23, Wherein the valve is movable into contact with the distal end of the catheter responsive to suction through the catheter.

25. The endotracheal suction catheter apparatus of claim 24, wherein the valve is pivotably disposed within the manifold.

26. The endotracheal suction catheter apparatus of claim 25, wherein the valve further comprises a ring disposed in the manifold, the single flap being pivotably attached to the ring by way of the biasing hinge.

27. The endotracheal suction catheter apparatus of claim 26, further comprising a projection attached to the ring and extending inwardly therefrom so as to selectively engage the single flap.

28. The endotracheal suction catheter apparatus of claim 27, wherein the projection is configured to enable movement of the single flap from an open, distal position to a closed, proximal position, but to inhibit movement of the single flap from the closed, proximal position to the open, distal position.

29. The endotracheal suction catheter apparatus of claim 23, wherein the single flap is disposed in the manifold and further comprises a means for holding the single flap to the distal end of the catheter.

30. The endotracheal suction catheter apparatus of claim 23, wherein the valve is disposed within the manifold.

31. A respiratory suction apparatus comprising:
    a suction catheter having a distal end for suctioning secretions;
    a protective sleeve surrounding a proximal longitudinal portion of the catheter;
    a manifold connected to the protective sleeve for attachment to a hub of an artificial airway in fluid communication between the respiratory tract of the patient and a ventilator, said manifold having means for accommodating inspiration and expiration of respiratory gases, and a lumen to accommodate advancement and retraction of the catheter through the manifold, the manifold having an introduction port for allowing the catheter to be introduced into the manifold, the introduction port having a longitudinal axis;
    a valve having a single flap, the valve connected to the manifold and pivotably moveable with respect thereto for engaging the distal end of the catheter to minimize the amount of air being drawn thereinto responsive to suction through the catheter, said valve capable of being actuated by suction through the catheter, the single flap being movable between a first, distal position and a second, proximal position in which the single flap is substantially perpendicular to the longitudinal axis of the introduction port of the manifold; and a biasing hinge biasing the single flap of the valve to the first distal position, the biasing hinge attached to the single flap and the manifold.

32. The respiratory suction apparatus according to claim 31, wherein said manifold having a first manifold lumen, and wherein the single flap is disposed to selectively separate the distal end of the catheter from the first manifold lumen and thereby substantially eliminate fluid flow between the distal end of the catheter and the first manifold lumen.

33. The respiratory suction apparatus according to claim 32, further comprising means for enhancing turbulence of the airflow.

34. An endotracheal catheter system comprising:

an elongated catheter having a proximal end and a distal end, said catheter having a tubular portion;

a fitting for connecting the elongated catheter to an artificial airway, the distal end of the catheter being advanceable through the fitting;

a cleaning chamber disposed adjacent the fitting, the cleaning chamber having a longitudinal axis, the catheter tube being advanceable through the cleaning chamber and retractable such that only the distal end of the catheter remains in the cleaning chamber, the cleaning chamber having a distal end with a self-closing valve comprising a single flap which is movable between open and closed positions, the valve substantially isolating the catheter from the fitting when in the closed position, in the closed position the single flap disposed substantially perpendicular to the longitudinal axis of the cleaning chamber, said valve capable of being opened by insertion of said tubular portion of said catheter into said fitting; and a biasing hinge biasing the single flap of the self-closing valve to the closed position, the biasing hinge attached to the cleaning chamber and the single flap.

35. The endotracheal catheter system of claim 34, wherein the self-closing valve closes when the distal end of the catheter passes by the valve while suction is being drawn through the catheter.

36. An endotracheal system comprising:

a manifold defining a portion of a ventilator circuit, the manifold having a passageway therethrough, the manifold having a port with a longitudinal axis;

a valve member comprising a single flap which is moveable between open and closed positions and which is disposed in the manifold, the valve member configured for substantially blocking the passageway of the manifold, in the closed position the single flap disposed substantially perpendicular to the longitudinal axis of the port of the manifold; and a biasing hinge biasing the single flap of the valve member to the closed position, the biasing hinge attached to the single flap.

37. The endotracheal system of claim 36, further comprising an elongated catheter having a tubular portion with a distal end, the catheter adapted to be moved through the manifold, the valve member disposed adjacent the catheter.

38. The endotracheal system of claim 37, wherein the valve member is movable between an open position wherein the valve member permits advancement of the catheter through the manifold, and a closed position wherein the valve member substantially isolates the catheter from the ventilator circuit.

39. An endotracheal system comprising:

a manifold defining a portion of a ventilator circuit, the manifold having a passageway therethrough;

a valve member comprising a single flap which is moveable between open and closed positions and which is disposed in the manifold, the valve member configured for substantially blocking the passageway of the manifold; and a biasing hinge biasing the single flap of the valve member to the open position, the biasing hinge attached to the single flap.

40. The endotracheal system of claim 39, further comprising an elongated catheter having a tubular portion with a distal end, the catheter adapted to be moved through the manifold, the valve member disposed adjacent the catheter.

41. The endotracheal system of claim 40, wherein the valve member is movable between an open position wherein the valve member permits advancement of the catheter through the manifold, and a closed position wherein the valve member substantially isolates the catheter from the ventilator circuit.

* * * * *

UNITED STATES PATENT AND TRADEMARK OFFICE
CERTIFICATE OF CORRECTION

PATENT NO. : 6,805,125 B1
DATED : October 19, 2004
INVENTOR(S) : Chet M. Crump, Edward B. Madsen and V. Roland Smith It is certified that error appears in the above-identified patent and that said Letters Patent is hereby corrected as shown below:

Column 24,
Line 14, the word "attached" should be replaced with -- integrally molded --.

Column 25,
Line 45, the statement "with a longitudinal axis" should be removed.

Column 26,
Line 6, the statement "the longitudinal axis of" should be removed.
Line 32, the word "attached" should be replace with -- integrally molded --.

Signed and Sealed this

Eighth Day of March, 2005

JON W. DUDAS
*Director of the United States Patent and Trademark Office*